(12) United States Patent
Farokhi et al.

(10) Patent No.: US 11,110,372 B2
(45) Date of Patent: Sep. 7, 2021

(54) COLD EXTRACTION METHOD FOR CANNABINOIDS AND TERPENES FROM CANNABIS BY ORGANIC SOLVENTS

(71) Applicant: Neptune Wellness Solutions Inc., Laval (CA)

(72) Inventors: Fereshteh Farokhi, Sherbrooke (CA); Pierre St-Jean, Laval (CA); Etienne Villeneuve, Laval (CA)

(73) Assignee: Neptune Wellness Solutions Inc., Laval (CA)

( * ) Notice: Subject to any disclaimer, the term of this patent is extended or adjusted under 35 U.S.C. 154(b) by 0 days.

(21) Appl. No.: 16/999,846

(22) Filed: Aug. 21, 2020

(65) Prior Publication Data

US 2020/0398184 A1 Dec. 24, 2020

Related U.S. Application Data

(63) Continuation of application No. PCT/CA2019/051090, filed on Aug. 8, 2019.

(60) Provisional application No. 62/716,195, filed on Aug. 8, 2018.

(51) Int. Cl.
| | |
|---|---|
| *A61K 36/185* | (2006.01) |
| *B01D 11/02* | (2006.01) |
| *A61K 31/05* | (2006.01) |
| *A61K 31/352* | (2006.01) |

(52) U.S. Cl.
CPC .......... *B01D 11/0288* (2013.01); *A61K 31/05* (2013.01); *A61K 31/352* (2013.01); *A61K 36/185* (2013.01); *B01D 11/0207* (2013.01); *B01D 11/0292* (2013.01); *A61K 2236/33* (2013.01); *A61K 2236/50* (2013.01)

(58) Field of Classification Search
None
See application file for complete search history.

(56) References Cited

U.S. PATENT DOCUMENTS

| | | | |
|---|---|---|---|
| 6,403,126 B1 * | 6/2002 | Webster | A61K 36/185 424/725 |
| 7,344,736 B2 | 3/2008 | Whittle et al. | |
| 7,700,368 B2 | 4/2010 | Flockhart et al. | |
| 2004/0156920 A1 | 8/2004 | Kane | |
| 2015/0297654 A1 * | 10/2015 | Speier | B01D 11/0407 424/725 |
| 2016/0213720 A1 | 7/2016 | Barringer | |
| 2017/0049830 A1 | 2/2017 | Raderman | |
| 2017/0095518 A1 * | 4/2017 | Bjorncrantz | A61K 9/007 |

FOREIGN PATENT DOCUMENTS

| | | |
|---|---|---|
| CA | 2612061 A1 | 12/2006 |
| CA | 2965493 A1 | 4/2016 |
| CA | 3038474 A1 | 4/2018 |
| EP | 2161262 A1 | 3/2010 |
| EP | 1385595 B1 | 5/2012 |
| GB | 635121 A | 4/1950 |
| WO | WO 99/11311 | 3/1999 |
| WO | WO 00/25127 | 5/2000 |
| WO | WO-2004016277 A2 * | 2/2004 ............. A61P 43/00 |
| WO | WO 2018/130682 | 7/2018 |
| WO | WO 2020/028991 | 2/2020 |
| WO | WO 2020/028992 | 2/2020 |
| WO | WO 2020/044118 | 3/2020 |

OTHER PUBLICATIONS

Ramirez et al. (2019) Studies in Natural Products Chemistry vol. 61: p. 143-173. (Year: 2019).*
ALCHIMIAweb, "Complete guide to solvent cannabis extracts," Alchimia Grow Shop blog, Mar. 2018, [Online] Retrieved on Sep. 5, 2019] <URL:https://www.alchimiaweb.com/blogen/complete-guide-solvent-cannabis-extracts/>, (2001), 16 pages.
Brenneisen, R., Chapter 2: "Chemistry and Analysis of Phytocannabinoids and Other Cannabis Constituents," In: Forensic Science and Medicine: Marijuana and the Cannabinoids, ElSohly, M. A. (ed.), Humana Press Inc., Totowa, New Jersey, (2007), pp. 17-49.
Brighenti, V. et al., "Development of a new extraction technique and HPLC method for the analysis of non-psychoactive cannabinoids in fibre-type *Cannabis sativa* L. (hemp)," Journal of Pharmaceutical and Biomedical Analysis, (Sep. 2017), vol. 143, pp. 228-236.
Buchbauer, G., Chapter 9: "Biological activities of essential oils," In: Baser, KHC and Buchbauer G (eds)., Handbook of Essential Oils: Science, Technology, and Applications. CRC Press: Boca Raton, FL, (2010), pp. 235-280.
Eisohly, M. A. et al., Chapter 3: "Chemical fingerprinting of cannabis as a means of source identification," In: Forensic Science and Medicine: Marijuana and the Cannabinoids, ElSohly, M. A. (ed.), Humana Press Inc., Totowa, New Jersey, (2007), pp. 51-66.
Langenheim, J. H., "Higher plant terpenoids: A phytocentric overview of their ecological roles," J Chem Ecol. (Jun. 1994), vol. 20, Issue 6, pp. 1223-1280. doi: 10.007/BF02059809.
Lewis, M. M. et al., "Chemical profiling of medical cannabis extracts," ACS Omega (Sep. 2017) vol. 2, Issue 9, pp. 6091-6103.
Pauli, A. et al., Chapter 12: "In vitro Antimicrobial Activities of Essential Oils Monographed in the European Pharmacopoeia 6th Edition," In: Baser, KHC and Buchbauer G (eds)., Handbook of Essential Oils: Science, Technology, and Applications. CRC Press: Boca Raton, FL, (2010), pp. 353-547.

(Continued)

*Primary Examiner* — Russell G Fiebig
(74) *Attorney, Agent, or Firm* — Cooley LLP; J. Dean Farmer; Cynthia A. Kozakiewicz

(57) ABSTRACT

The invention relates to methods of producing extracts from *cannabis* plant material, where the extracts comprise cannabinoids and terpenes. The methods comprise extracting fresh or dried plant material with a cold organic solvent. The methods allow for the extraction of cannabinoids and terpenes, while leaving behind impurities such as waxes and chlorophyll that are commonly found in extractions with room temperature (RT) or warm solvent extraction methods. The methods can produce extracts having more than 90% cannabinoids.

20 Claims, 5 Drawing Sheets

(56) References Cited

OTHER PUBLICATIONS

Yang, Y. et al., "*Cannabis sativa* (Hemp) seeds, $\Delta^9$-tetrahydrocannabinol, and potential overdose," Cannabis and Cannabinoid Research, (2017), vol. 2, Issue 1, pp. 274-281.

Lumen, "Factors Affecting Solubility," Boundless Chemistry [Online], Retrieved from the Internet: <https://courses.lumenlearning.com/boundless-chemistry/chapter/factors-affecting-solubility/>, Retrieved on Apr. 23, 2021, 12 pages.

Wikipedia, "Hashish", [Online], Retrieved from the Internet: <https://en.wikipedia.org/wiki/Hashish>, Retrieved on Apr. 23, 2021, 8 pages.

\* cited by examiner

COLD EXTRACTION METHOD FOR CANNABINOIDS AND TERPENES FROM CANNABIS BY ORGANIC SOLVENTS

RELATED APPLICATIONS

This application is a continuation of International Application No. PCT/CA2019/051090, filed on Aug. 8, 2019, which claims priority to and benefit of U.S. Provisional Application No. 62/716,195, filed on Aug. 8, 2018, the contents of each of which are incorporated herein in their entirety.

FIELD OF THE INVENTION

The present invention relates generally to methods of extracting cannabinoids, flavonoids, terpenes and other bioactive molecules from plants of the *Cannabis* genus and the botanical extracts produced using these methods. These methods comprise extracting and isolating compounds from *cannabis* plants at low temperature using cold organic solvents, such as acetone and ethanol.

BACKGROUND OF THE INVENTION

*Cannabis* has traditionally been used medicinally, especially as a mild analgesic and tranquilizer, but different conventional agents have replaced its use, and controlled prescribing was discontinued.

In recent times, *cannabis* has been shown to have valuable anti-emetic properties that help reduce the side-effects of nausea and vomiting caused by cancer chemotherapeutic agents. *Cannabis* has also been shown to possess properties that may be of value in other medical conditions. There is now scientific evidence that *cannabis* may give relief to patients suffering from chronic pain, multiple sclerosis, glaucoma, asthma, migraine, epilepsy, and other conditions. The non-intoxicating cannabinoid, cannabidiol (CBD), has been shown to have anti-inflammatory properties that can be potentially useful in the treatment of symptoms of arthritis.

A need exists for a method of extracting cannabinoids, terpenes and other compounds from *cannabis* to resolve the problems of other prior techniques, such as efficiency, selectivity, onerous extraction methods, and unwanted contaminants in the final product. The present invention solves these problems.

SUMMARY OF THE INVENTION

The disclosure provides methods of preparing botanical extracts and the botanical extracts obtained therefrom.

The disclosure provides methods of preparing botanical extracts comprising: providing plant material in an extraction chamber; releasing organic solvent from a solvent chamber into the extraction chamber; extracting a bioactive molecule from the plant material into the organic solvent for a first period of time; filtering the organic extract from the plant material; and recovering the compounds from the organic solvent by evaporation thereby producing a botanical extract.

The disclosure provides methods of preparing botanical extracts comprising: (a) providing a plant material in an extraction chamber; (b) contacting an organic solvent with the plant material; (c) extracting at least one bioactive molecule from the plant material into the organic solvent for a first period of time, thereby producing an organic solvent comprising a botanical extract; (d) filtering the organic solvent comprising a botanical extract from the extraction chamber using a cold filtration/centrifugation system; and (e) recovering the botanical extract from the organic solvent; thereby producing a botanical extract.

In some embodiments of the methods of the disclosure, contacting the organic solvent with the plant material comprises releasing the organic solvent from a solvent chamber into the extraction chamber.

In some embodiments of the methods of the disclosure, the plant material is heated prior to placing it into the extraction chamber (step (a)). In some embodiments, the plant material is heated to a temperature of about between 110° C. to 145° C. In some embodiments, the plant material is heated to a temperature of about between 115° C. to 145° C. In some embodiments, the plant material is heated for about 40 to 75 minutes.

In some embodiments of the methods of the disclosure, the first period of time at step (c) is no more than 1 hour. In some embodiments, the first period of time is between about 5 and 45 minutes, between about 5 and 30 minutes, between about 10 and 45 minutes, between about 10 and 30 minutes or between about 10 and 20 minutes. In some embodiments, the first period of time is about 15, 20, 30, or 50 minutes.

In some embodiments of the methods of the disclosure, the methods comprise agitating the organic solvent and the plant material during step (c). In some embodiments, the contents are agitated during all or part of the first period of time.

In some embodiments of the methods of the disclosure, the methods comprise sonicating the organic solvent and the plant material for a second period of time. In some embodiments, the methods comprise sonicating during all of the first period of time, or for a specified second period of time. In some embodiments, the first and second period of time are the same. In some embodiments, the sonication occurs prior to step (c). In some embodiments, the second period of time is about 10 minutes.

In some embodiments of the methods of the disclosure, the organic solvent is at a temperature of about between 0° C. to −80° C. In some embodiments, the organic solvent is at a temperature of between about 0° C. and −70° C., about 0° C. and −60° C., about 0° C. and −50° C., about 0° C. and −40° C., about 0° C. and −30° C., about 0° C. and −20° C., about 0° C. and −10° C., about −10° C. and −80° C., about −10° C. and −60° C., about −10° C. and −50° C., about −10° C. and −40° C., about −20° C. and −60° C., or about −20° C. and −50° C.

In some embodiments of the methods of the disclosure, the organic solvent is any class 3 solvent. In some embodiments, the organic solvent is selected from the group consisting of ethanol, acetone, and ethyl acetate.

In some embodiments of the methods of the disclosure, the methods comprise returning the organic solvent comprising the botanical extract from step (d) to the extraction chamber and repeating steps (b) through (d). In some embodiments, steps (b) through (d) are repeated 2×, 3×, 4×, 5×, 6×, 7×, 8×, 9×, or 10×. In some embodiments, unextracted plant material is added to the extraction chamber prior to repeating steps (c) and (d).

In some embodiments of the methods of the disclosure, step (e) comprises evaporation of the organic solvent.

In some embodiments of the methods of the disclosure, the botanical extract is subject to one or more additional purification methods. In some embodiments, the one or more additional purification methods comprise molecular distillation or high-performance liquid chromatography (HPLC).

In some embodiments of the methods of the disclosure, the plant material is fresh or dried. In some embodiments, the plant material is intact or milled.

In some embodiments of the methods of the disclosure, the plant material is *cannabis*. In some embodiments, the *cannabis* is *Cannabis sativa, Cannabis indica* or *Cannabis ruderalis*. In some embodiments, the *cannabis* is a hybrid. In some embodiments, the hybrid is derived from species or varieties of the *cannabis* plant. In embodiments, the *cannabis* is industrial hemp.

In some embodiments of the methods of the disclosure, the methods comprise de-waxing. In some embodiments, the de-waxing comprises filtering the organic solvent comprising the botanical extract.

In some embodiments of the methods of the disclosure, the at least one bioactive molecule comprises a cannabinoid, a flavonoid or a terpene. In some embodiments, the cannabinoid comprises $\Delta^9$ tetrahydrocannabinol (THC), cannabidiol (CBD), tetrahydrocannabinolic acid (THCA), cannabidiolic acid (CBDA), cannabigerolic acid (CBGA), cannabichromenenic acid (CBCA), cannabigerovarinic acid (CBGVA), tetrahydrocanabivarinic acid (THCVA), cannabidivarinic acid (CBDVA), cannabichromevarinic acid (CBCVA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethylether (CBGM), cannabielsoin (CBE), cannabicitran (CBT), or a combination thereof. In some embodiments, the cannabinoid comprises THC, THCA, CBD, CBDA or a combination thereof. In some embodiments, the cannabinoid comprises a combination of THC and CBD. In some embodiments, the terpene comprises myrcene, terpinolene, β-caryophyllene, selina-3 7(11)-diene, guaiol, 10-epi-y-eudesmol, β-eudesmol, α-eudesmol, bulnesol, α-bisabolol or a combination thereof.

The disclosure provides botanical extracts produced by the methods of the disclosure.

In some embodiments of the botanical extracts of the disclosure, the botanical extract is a liquid. In some embodiments, the botanical extract is a resin.

The disclosure provides botanical extracts comprising at least one cannabinoid and an organic solvent.

In some embodiments of the botanical extracts of the disclosure, the organic solvent is selected from the group consisting of ethanol, acetone and ethyl acetate.

The disclosure provides compositions comprising the botanical extracts of the disclosure and a pharmaceutically acceptable carrier, diluent or excipient.

In some embodiments of the compositions of the disclosure, the composition is formulated for oral administration. In some embodiments, the composition is formulated as a liquid, gel, softgel, powder, tablet, caplet, capsule, gelcap, food additive, drop, beverage, pill, lozenge, rinse, paste or gum.

In some embodiments of the compositions of the disclosure, the composition is formulated for topical administration. In some embodiments, the composition is formulated as a liquid, gel, cream, ointment, lotion, salve, balm or paste.

In some embodiments of the compositions of the disclosure, the composition is formulated for transmucosal administration, parenteral administration, subdermal administration, or inhalation. In some embodiments, the transmucosal administration comprises buccal administration or intra-nasal administration.

The disclosure provides methods of making a *cannabis* extract composition, comprising: (a) providing the botanical extract produced by the methods of disclosure, and (b) mixing the botanical extract with a pharmaceutically acceptable carrier, diluent or excipient.

In some embodiments of the methods of making *cannabis* extract compositions of the disclosure, the composition is formulated for oral administration. In some embodiments, the composition is formulated as a liquid, gel, softgel, powder, tablet, caplet, capsule, gelcap, food additive, drop, beverage, pill, lozenge, rinse, paste or gum.

In some embodiments of the methods of making *cannabis* extract compositions of the disclosure, the composition is formulated for topical administration. In some embodiments, the composition is formulated as a liquid, gel, cream, ointment, lotion, salve, balm or paste.

In some embodiments of the methods of making *cannabis* extract compositions of the disclosure, the composition is formulated for transmucosal administration, parenteral administration, subdermal administration, or inhalation. In some embodiments, the transmucosal administration comprises buccal administration or intra-nasal administration.

Unless otherwise defined, all technical and scientific terms used herein have the same meaning as commonly understood by one of ordinary skill in the art to which this invention belongs. In the specification, the singular forms also include the plural unless the context clearly dictates otherwise. Although methods and materials similar or equivalent to those described herein can be used in the practice or testing of the present invention, suitable methods and materials are described below. In the case of conflict, the present specification, including definitions, will control. In addition, the materials, methods and examples are illustrative only and are not intended to be limiting.

Other features and advantages of the invention will be apparent from the following detailed description and claims.

DETAILED DESCRIPTION OF THE INVENTION

Figure 1:
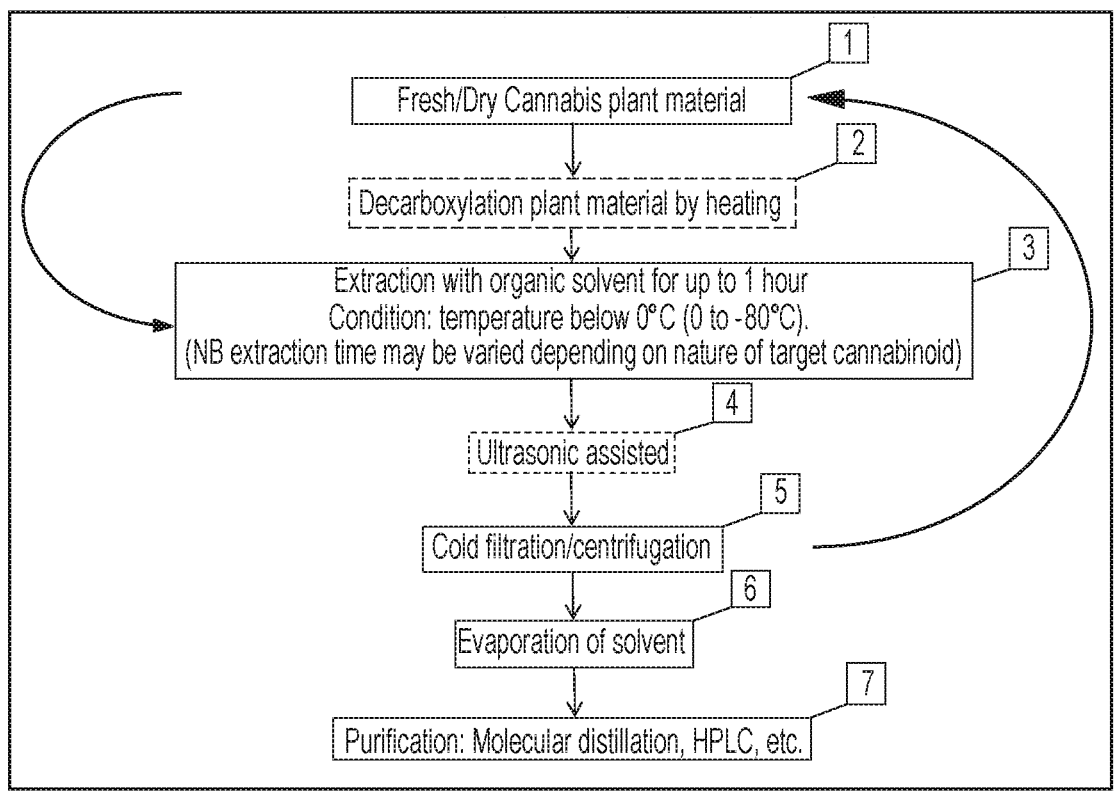
FIG. 1 is a flow diagram illustrating cold organic-based extraction of cannabinoids and terpenes from the *cannabis* plant in accordance with the methods of the disclosure.
Figure 2:
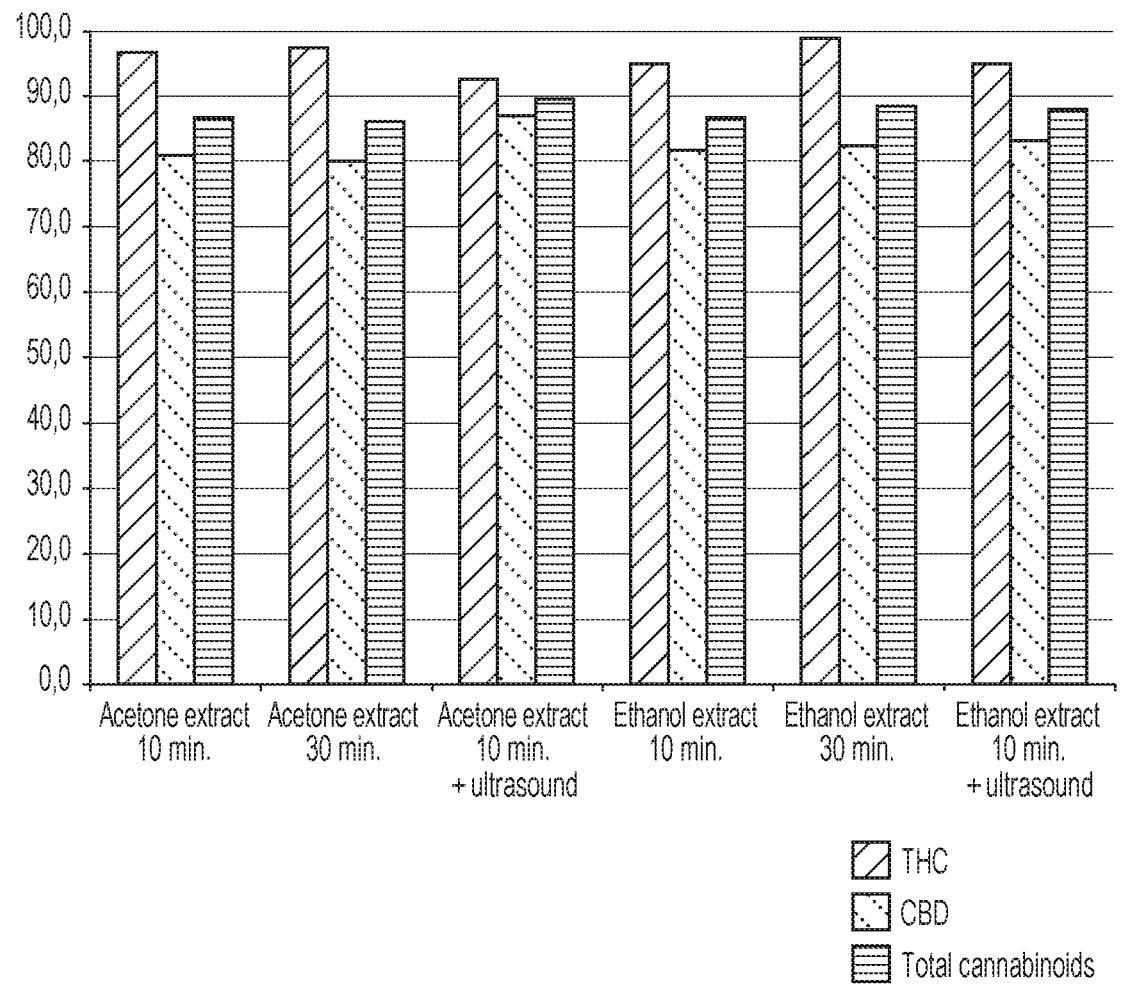
FIG. 2 is a plot showing acetone and ethanol cold extraction efficiencies (%) for Total THC (THCA+THC), Total CBD (CBDA+CBD), and total cannabinoids on dry, cold, ground *cannabis* material. Extract results (%) are compared to control extraction with Methanol/Chloroform (9:1). THC, $\Delta^9$-tetrahydrocannabinol; THCA, $\Delta^9$-tetrahydrocannabinolic acid; CBD, cannabidiol; CBDA, cannabidiolic acid.
Figure 3:
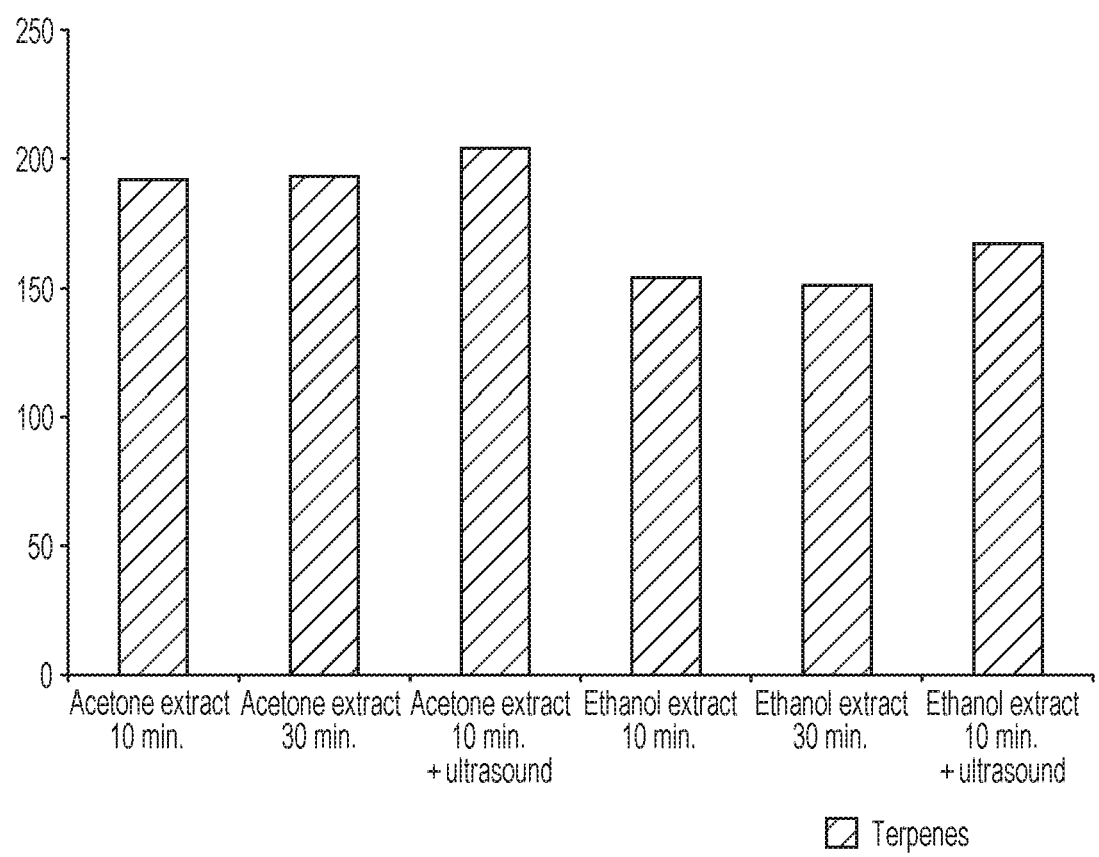
FIG. 3 is a plot showing acetone and ethanol cold extraction efficiencies (%) for terpenes on dry, cold, ground *cannabis* material.
Figure 4:
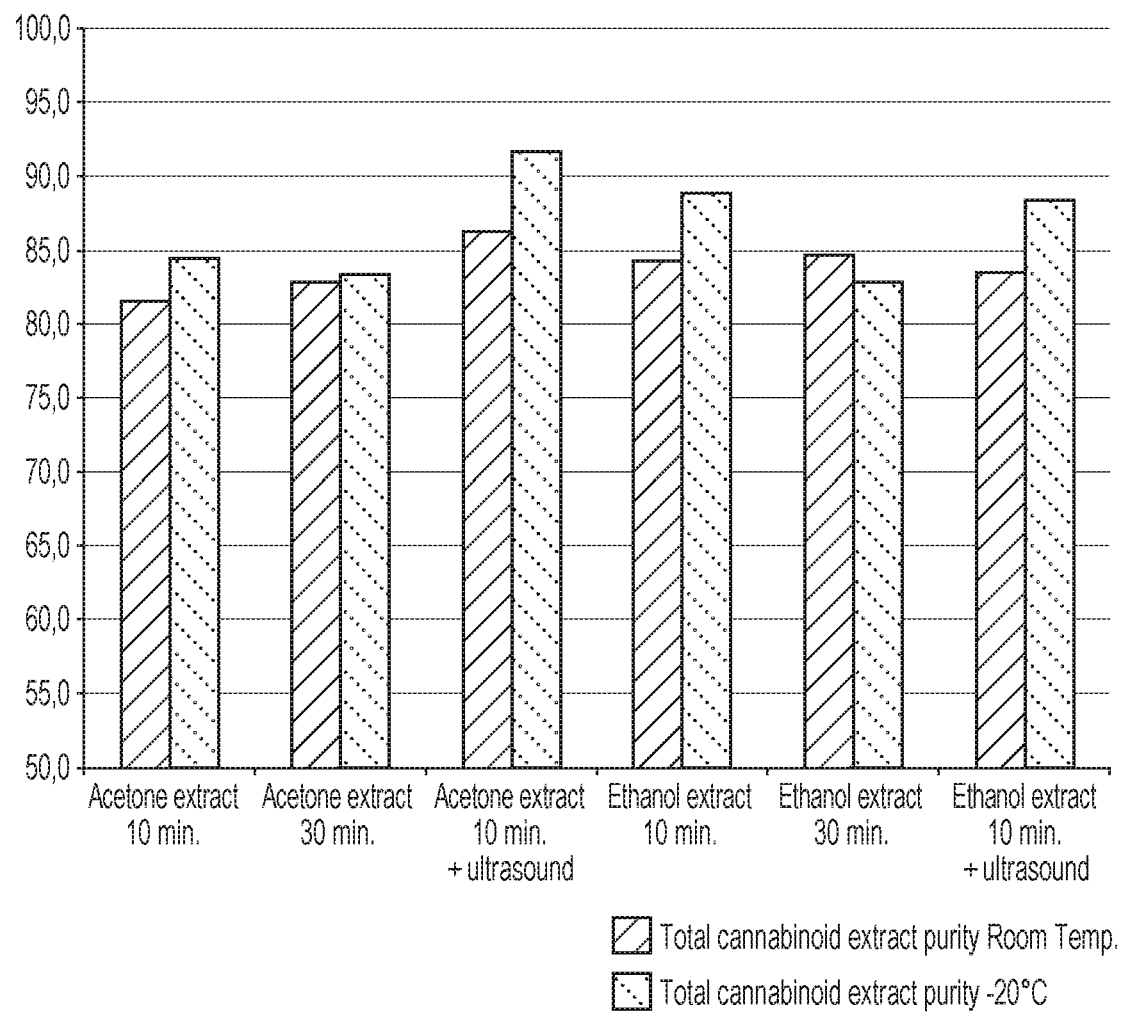
FIG. 4 is a plot showing the purity (%) of the acetone and ethanol extracts at −20° C. compared to room temperature (RT).
Figure 5:
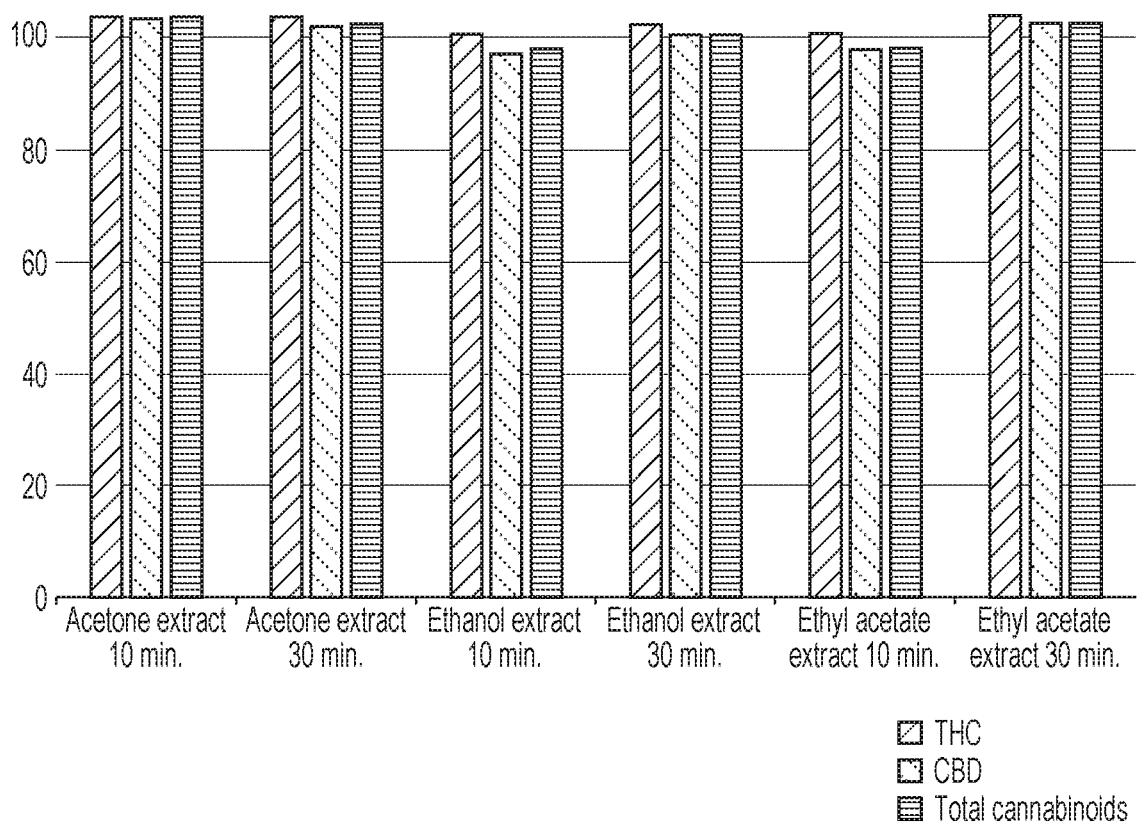
FIG. 5 is a plot showing acetone, ethanol and ethyl acetate cold extraction efficiencies (%) for Total THC, Total CBD, and Total cannabinoids on dry, cold, ground decarboxylated *cannabis* material. Extract results (expressed as neutral form) are compared (%) to control extraction with Methanol/Chloroform (9:1). Acetone, Ethanol and Ethyl Acetate cold extraction efficiencies (%) for Total THC, Total CBD and Total cannabinoids on dry cold ground decarboxylated *cannabis* material. Extract results are compared to a control extraction performed with Methanol/Chloroform (9:1) on the same material at RT.

The invention relates to an extraction process of bioactive compounds from plant material. More specifically, the invention provides methods for extracting and isolating compounds such as pure cannabinoids, cannabinoid acids, terpenes, terpenoids, or flavonoids from *cannabis* plant material at low temperature by using cold organic solvent.

The extraction process of the invention maximizes extraction efficiency and minimizes contaminants and impurities, such as waxes and chlorophyll.

*Cannabis*

*Cannabis* is a genus of plants that include three species, *Cannabis sativa*, *Cannabis indica*, and *Cannabis ruderalis*. More generally, *cannabis* also is categorized as either marijuana or hemp based on the natural amount of $\Delta^9$-tetrahydrocannabinol (THC) present in the plant material, with marijuana being high in THC and hemp having negligible to no amount of THC. This genus has long been in use for its hemp fiber material, as milk, seeds and oils, for medicinal purposes, and for recreational use. *Cannabis* species contain a highly complex mixture of compounds, and up to 568 unique molecules have been identified to date (Lewis, M. M. et al., Chemical Profiling of Medical *Cannabis* Extracts, ACS Omega (2017) 2(9): 6091-6103), any one of which are potentially bioactive in humans. Exemplary bioactive molecules in *cannabis* comprise cannabinoids, terpenes and flavonoids.

A variety of strains and hybrids of *Cannabis* will be known to the person of ordinary skill in the art, all of which can be used as starting material to produce botanical extracts using the methods of the instant invention. Different *Cannabis* strains produce different amounts of various cannabinoids and/or terpenes, and choice of *Cannabis* strain(s) or hybrid(s) can contribute to the cannabinoid and/or terpene composition of the botanical extracts produced using the methods described herein. The person of ordinary skill in the art will be able to select the starting *Cannabis* strain or hybrid most suited to the desired cannabinoid and/or terpene composition of the resulting botanical extract. For example, high cannabidiol (CBD) strains include Charlotte's Web, Cannatonic, AC/DC, Harlequin, Ringo's Gift, Harle-Tsu, Nebula and Sour Tsunami. Exemplary high $\Delta^9$-tetrahydrocannabinol (THC) strains include Girl Scout Cookies (GSC), Kosher Kush, Ghost OG, Bruce Banner, Ghost Train Haze, Chemdawg, Ace of Spades, Afghani, Afgoo, AK-47, Alien OG, Alien Rock Candy, Allen Wrench, Animal Cookies, Sour Diesel, Skywalker, GG4, The White, Death Star, White Fire OG, Kimbo Kush, Headband, Cherry Pie, Bubba Kush, SFV OG, LA Confidential and Triangle Kush. An exemplary high tetrahydrocannabivarin (THCV) strain includes Dutch Treat.

Any part of the *Cannabis* plant may be used in the extraction methods of the instant disclosure. For example, stems, leaves, seeds, flowers or a combination thereof can be used as the starting material for the extraction methods of the invention. In some aspects, one or more parts of the plant are used in practicing the claimed methods. Alternatively, all parts of the plants may be used in practicing the claimed methods.

Cannabinoids

In some embodiments, the instant disclosure provides methods of producing botanical extracts comprising cannabinoids, and compositions comprising botanical extracts comprising cannabinoids.

Cannabinoids are a class of chemical compounds that act on the cannabinoid receptors, also known as the endocannabinoid system in cells. Cannabinoids include endocannabinoids, produced naturally in the body by animals; phytocannabinoids, produced by *Cannabis* and other plants; and synthetic cannabinoids, which are manufactured. Phytocannabinoids, sometimes also referred to herein as cannabinoids, are a structurally diverse class of molecules that are derived from a common C21 precursor (cannabigerolic acid, or CBGA) or its C19 analog (cannabigerovaric acid, or CBGVA).

There are currently over 100 cannabinoids known to be produced by *Cannabis* plants, all of which can be purified using the methods of the instant disclosure. Cannabinoids are described in, for example, Brenneisen R. (2007) Chemistry and Analysis of Phytocannabinoids and Other *Cannabis* Constituents. In: ElSohly M. A. (eds) Marijuana and the Cannabinoids. Forensic Science and Medicine; Humana Press; pp. 17-49. Exemplary cannabinoids include Cannabichromenes such as Cannabichromene (CBC), Cannabichromenic acid (CBCA), Cannabichromevarin (CBCV) and Cannabichromevarinic acid (CBCVA); Cannabicyclols such as Cannabicyclol (CBL), Cannabicyclolic acid (CBLA) and Cannabicyclovarin (CBLV); Cannabidiols such as Cannabidiol (CBD), Cannabidiol monomethylether (CBDM), Cannabidiolic acid (CBDA), Cannabidiorcol (CBD-C1), Cannabidivarin (CBDV) and Cannabidivarinic acid (CBDVA); Cannabielsoins such as Cannabielsoic acid B (CBEA-B), Cannabielsoin (CBE) and Cannabielsoin acid A (CBEA-A); Cannabigerols such as Cannabigerol (CBG), Cannabigerol monomethylether (CBGM), Cannabigerolic acid (CBGA), Cannabigerolic acid monomethylether (CBGAM), Cannabigerovarin (CBGV) and Cannabigerovarinic acid (CBGVA); Cannabinols and cannabinodiols such as Cannabinodiol (CBND), Cannabinodivarin (CBVD), Cannabinol (CBN), Cannabinol methylether (CBNM), Cannabinol-C2 (CBN-C2), Cannabinol-C4 (CBN-C4), Cannabinolic acid (CBNA), Cannabiorcool (CBN-C1) and Cannabivarin (CBV); Cannabitriols such as 10-Ethoxy-9-hydroxy-delta-6a-tetrahydrocannabinol, 8,9-Dihydroxy-delta-6a-tetrahydrocannabinol, Cannabitriol (CBT) and Cannabitriolvarin (CBTV); Delta-8-tetrahydrocannabinols such as Delta-8-tetrahydrocannabinol ($\Delta^8$-THC) and Delta-8-tetrahydrocannabinolic acid (Ae-THCA); Delta-9-tetrahydrocannabinols such as Delta-9-tetrahydrocannabinol (THC), Delta-9-tetrahydrocannabinol-C4 (THC-C4), Delta-9-tetrahydrocannabinolic acid A (THCA-A), Delta-9-tetrahydrocannabinolic acid B (THCA-B), Delta-9-tetrahydrocannabinolic acid-C4 (THCA-C4), Delta-9-tetrahydrocannabiorcol (THC-C1), Delta-9-tetrahydrocannabiorcolic acid (THCA-C1), Delta-9-tetrahydrocannabivarin (THCV) and Delta-9-tetrahydrocannabivarinic acid (THCVA); as well as 10-Oxo-delta-6a-tetrahydrocannabinol (OTHC), Cannabichromanon (CBCF), Cannabifuran (CBF), Cannabiglendol, Cannabiripsol (CBR), Cannbicitran (CBT), Dehydrocannabifuran (DCBF), Delta-9-cis-tetrahydrocannabinol (cis-THC), Tryhydroxy-delta-9-tetrahydrocannabinol (triOH-THC) and 3,4,5,6-Tetrahydro-7-hydroxy-alpha-alpha-2-trimethyl-9-n-propyl-2,6-methano-2H-1-benzoxocin-5-methanol (OH-iso-HHCV).

The principle cannabinoid components present in plants of the *cannabis* species are the cannabinoid acids, $\Delta^9$-tetrahydrocannabinolic acid ($\Delta^9$-THCA or THCA) and cannabidiolic acid (CBDA), with small amounts of the corresponding neutral cannabinoids, respectively, i.e., $\Delta^9$-tetrahydrocannabinol ($\Delta^9$-THC or THC) and cannabidiol (CBD). Other cannabinoid acids include: CBGA (cannabigerolic acid), CBCA (cannabichromenenic acid), CBGVA (cannabigerovarinic acid), THCVA (tetrahydrocanabivarinic acid), CBDVA (cannabidivarinic acid), and CBCVA (cannabichromevarinic acid).

Other neutral cannabinoids include CBN (cannabinol), CBG (cannabigerol), CBC (cannabichromene), CBL (cannabicyclol), CBV (cannabivarin), THCV (tetrahydrocannabivarin), CBDV (cannabidivarin), CBCV (cannabichromevarin), CBGV (cannabigerovarin), CBGM (cannabigerol monomethylether), CBE (cannabielsoin), and CBT (cannabicitran).

Terpenes

In some embodiments, the instant disclosure provides methods of producing a botanical extract comprising terpenes. In some embodiments, the botanical extract comprises terpenes and cannabinoids. In some embodiments, the botanical extract comprises terpenes, cannabinoids and flavonoids.

Terpenes, sometimes referred to as terpenoids, are essential oil (EO) components present in numerous botanicals, and form the largest group of plant chemicals, with 15-20,000 terpenes that have been fully characterized (Langenheim JH. Higher plant terpenoids: A phytocentric overview of their ecological roles. J Chem Ecol. 1994 June; 20(6): 1223-80. doi: 10.1007/BF02059809). Terpenes comprise a large group of compounds synthesized from $C_{10}$ isoprene subunits. The European pharmacopoeia, Sixth Edition (2007), lists 28 EOs (Pauli A, Schilcher H (2010). In vitroantimicrobial activities of essential oils monographed in the European Pharmacopoeia 6th Edition. In: Baser KHC, Buchbauer G (eds). Handbook of Essential Oils: Science, Technology, and Applications. CRC Press: Boca Raton, Fla., pp. 353-548). Terpenoids are pharmacologically versatile: they are lipophilic, interact with cell membranes, neuronal and muscle ion channels, neurotransmitter receptors, G-protein coupled (odorant) receptors, second messenger systems, and enzymes (Bowles, E. J., 2003. Chemistry of Aromatherapeutic Oils. Allen & Unwin, ISBN 174114051X; Buchbauer G. Biological activities of essential oils. In: Baser KHC, Buchbauer G, editors. Handbook of Essential Oils: Science, Technology, and Applications. Boca Raton, Fla.: CRC Press; 2010. pp. 235-280). It is not surprising that cannabinoids are produced with terpenoid compounds. Monoterpenes ($C_{10}$) and sesquiterpenes (Cis) are the classes most commonly identified in *Cannabis* spp. Terpenoids are the primary aromatic constituents of *cannabis* resin, although they constitute only a small percentage of organic solvent extracts (Elsohly et al. Chemical fingerprinting of *cannabis* as a means of source identification. Marijuana and cannabinoids pp 51-66. Humana press. 2007).

Without wishing to be bound by theory, it is thought that interplay between the effects of cannabinoids and other compounds derived from *Cannabis* such as terpenes and/or flavonoids, sometimes referred to as the "entourage effect" can enhance the efficacy of *Cannabis* extracts for the treatment of a variety of diseases and disorders. For example, it is thought that the terpene myrcene can enhance penetration across the blood brain barrier, pinene can counteract memory and cognition problems, while the combination of pinene, myrcene, and caryophyllene can help treat anxiety.

There are currently at least 80-100 terpenes found in *Cannabis*. Exemplary terpenes produced by *Cannabis* that can be extracted using the methods described herein comprise Limonene, Nerolidol, Phytol, Caryophyllene Oxide, Linalool, α-pinene, β-pinene, Eucalyptol, Trans-nerolido, Humulene, delta-3-carene, Camphene, Borneol, Valencene, Geraniol, Myrcene, Terpinolene, β-caryophyllene, selina-3 7(11)-diene, guaiol, 10-epi-y-Eudesmol, β-Eudesmol, α-Eudesmol, Bulnesol, α-Bisabolol, or a combination of any of these. In some embodiments, terpenes extracted using the methods described herein comprise Myrcene, Terpinolene, β-caryophyllene, selina-3 7(11)-diene, guaiol, 10-epi-y-Eudesmol, β-Eudesmol, α-Eudesmol, Bulnesol, α-Bisabolol, or a combination of any of these.

Different *Cannabis* strains or varieties contain different terpene compositions. For example, strains such as Super Silver Haze, Skywalker and Rock Star produce of beta-caryophyllene. As a further example, strains such as Jack Herer, Strawberry Cough, Blue Dream, Island Sweet Skunk, Dutch Treat and Romulan produce pinenes. As a further example, strains such as Skunk XL, White Widow, and Special Kush produce myrcene. As yet a further example, strains such as Harle-Tsu, Pink Kush, Headband, OG Shark, and ACDC produce α-Bisabolol. The person of ordinary skill will be able to select a *Cannabis* strain producing the desired terpene(s) for use with the extraction methods disclosed herein.

Flavonoids

In some embodiments, the instant disclosure provides methods of producing a botanical extract comprising flavonoids. In some embodiments, the botanical extract comprises flavonoids and cannabinoids. In some embodiments, the botanical extract comprises flavonoids, terpenes and cannabinoids.

Flavonoids are secondary polyphenolic metabolites that commonly have a ketone group and yellowish pigments. In *Cannabis*, at least 20 flavonoids have been identified, mainly belonging to flavone and flavonol subclasses. Without wishing to be bound by theory, it is though that the flavonoids in *Cannabis* can exert a wide range of biological effects, including aiding in the efficacy of *Cannabis* extracts for the treatment of diseases or disorders through the entourage effect.

Exemplary flavonoids that can be extracted using the methods of the instant disclosure include, but are not limited to, cannflavin A, cannflavin B, cannflavin C, vitexin, isovitexin, apigenin, kaempferol, quercetin, luteolin, orientin or a combination of any of these.

Extraction Methods

*Cannabis* extracts are traditionally made by exposing *cannabis* plants to butane, propane, carbon dioxide and/or other solvents to leach the compounds from *cannabis* plants. But each of these methods has different disadvantages. For example, in the butane hash oil (BHO) extraction method, cooled butane (a toxic solvent) is passed through a dried herbal material under pressure and allowed to expand as it is released from its storage vessel and cools into a liquid with a temperature below 0° C. However, because of its non-polar solvent properties, butane extracts hydrophobic constituents, such as plant waxes. In the supercritical carbon dioxide ($CO_2$) extraction method, $CO_2$ is used as a solvent at a temperature and pressure above the critical point, 304.25K and 72.9 atm, respectively, as a solvent. But because of the high pressures required to achieve a supercritical state for $CO_2$, the impurities such as waxes, chlorophyll, etc., will be extracted into the final extract material.

The extraction process of the invention is useful for the production of *cannabis* extracts, whether from marijuana or hemp. The methods of the instant disclosure allow for the production of extracts having more than 75%, more than 80%, more than 90%, more than 95%, more than 96%, more than 97%, more than 98%, more than 98%, more than 99% or more total cannabinoids.

Accordingly, the disclosure provides methods of preparing a botanical extract comprising (a) providing a plant material; (b) contacting an organic solvent with the plant material; (c) extracting at least one bioactive molecule from the plant material into the organic solvent, thereby producing an organic solvent comprising a botanical extract; (d) filtering the organic solvent comprising a botanical extract; and (e) recovering the botanical extract from the organic solvent; thereby producing a botanical extract. In some embodiments, step (c), the extraction step, takes place at between 0° C. and −80° C. In some embodiments, step (c), the extraction step, takes place at between −20° C. and −50° C.

In some embodiments, the methods of preparing a botanical extract comprise (a) providing a plant material in an extraction chamber; (b) contacting an organic solvent with the plant material; (c) extracting at least one bioactive molecule from the plant material into the organic solvent for a first period of time, thereby producing an organic solvent comprising a botanical extract; (d) filtering the organic solvent comprising a botanical extract from the extraction chamber into a cold filtration/centrifugation system; and (e) recovering the botanical extract from the organic solvent; thereby producing a botanical extract. In some embodiments, step (c), the extraction step, takes place at between 0° C. and −80° C. In some embodiments, step (c), the extraction step, takes place at between −20° C. and −50° C.

The process of the invention utilizes organic solvent at cold temperatures (0° C. to −80° C.). Benefits of this method/technique described herein include, but are not limited to, one or more of the following (or combinations thereof): it is significantly less expensive and more efficient than supercritical fluid extraction; it is materially safer than extractions using other organic solvents; it is faster and safer than traditional methods; it results in a final extract with significantly less impurities, such as waxes and chlorophyll, than traditional methods; it is capable of producing significantly more potent end products than traditional methods.

In some embodiments, the organic solvent, and the extraction step, are at a temperature of between about 0° C. and −70° C., about 0° C. and −60° C., about 0° C. and −50° C., about 0° C. and −40° C., about 0° C. and −30° C., about 0° C. and −20° C., about 0° C. and −10° C., about −10° C. and −80° C., about −10° C. and −60° C., about −10° C. and −50° C., about −10° C. and −40° C., about −20° C. and −60° C., or about −20° C. and −50° C. In some embodiments, the organic solvent, and the extraction step, are at a temperature of about −10° C., about −20° C., about −30° C., about −40° C., about −50° C., about −60° C., about −70° C., or about −80° C. In some embodiments, the organic solvent, and the extraction step, are at a temperature of about −20° C. In some embodiments, the organic solvent, and the extraction step, are at a temperature of about −50° C.

In some embodiments, the organic solvent comprises any class 3 organic solvent. Class 3 solvents are solvents that are classified as solvents with low toxic potential, low toxic potential to humans, for which no health-based exposure limit is needed. Class 3 toxic solvents have a permissible daily exposure of 50 milligrams or more per day. Exemplary class 3 solvents include, but are not limited to, Acetic acid, Heptane, Acetone, Isobutyl acetate, Anisole, Isopropyl acetate, 1-Butanol, Methyl acetate, 2-Butanol, 3-Methyl-1-butanol, Butyl acetate, Methylethylketone, tert-Butylmethyl ether, Methylisobutylketone, Cumene, 2-Methyl-1-propanol, Dimethyl sulfoxide, Pentane, Ethanol, 1-Pentanol, Ethyl acetate, 1-Propanol, Ethyl ether, 2-Propanol, Ethyl formate, Propyl acetate and Formic acid. In some embodiments, the organic solvent comprises ethanol, acetone, or ethyl acetate.

Various steps for producing *cannabis* extract are described below. It will be understood that certain steps described can be optional and that the order of steps may vary.

FIG. 1 is a flow chart of cold organic-based extraction of cannabinoids and terpenes from *cannabis*. The method starts, in step 1, whereby plant material is placed within an extraction chamber. In some embodiments, the extraction chamber is part of a two chambered extractor comprising an extraction chamber into which the plant material is placed, and a solvent chamber that contains organic solvent. In some embodiments, the solvent chamber maintains the organic solvent a cold temperature, for example between 0° C. and −50° C. The cold organic solvent flows from the solvent reservoir into the extraction chamber, where the solvent is exposed to and washes through the plant material. This dissolves and carries away the extractable compounds from the plant material. The time of exposure of *cannabis* material to solvent can be short (up to 60 minutes). In some embodiments, the extraction period is between about 5 and 45 minutes, between about 5 and 30 minutes, between about 10 and 45 minutes, between about 10 and 30 minutes or between about 10 and 20 minutes. In some embodiments, the extraction period is 10 minutes. In some embodiments, the extraction period is 30 minutes.

In embodiments of the method where it is desired to purify neutral cannabinoids such as THC, CBD, CBN, CBG and CBC, rather than the cannabinoid acids such as THCA, CBDA, CBGA and CBCA, the plant material may be subjected to a decarboxylation step, step 2, prior to step 3 of FIG. 1. The purpose of the decarboxylation step is to convert cannabinoid acids present in the plant material to the neutral cannabinoids. Decarboxylation of cannabinoid acids is a function of time and temperature, thus at higher temperatures a shorter period of time will be taken to complete decarboxylation of a given amount of cannabinoid acid. Suitable conditions may include, for example, a temperature in the range of 135 to 145° C. for a time period in the range of 15 to 40 minutes or from 110° C. to 125° C. for a time period in the range of 40 to 75 minutes. Suitable conditions may include 110° C. to 145° C. for a time period in the range of 40 to 75 minutes.

Ultrasound also can be used in an attempt to liberate the cannabinoids from the *cannabis* plant, step 4 of FIG. 1. Ultrasound can be produced using sonication. Sonication applies intense shear forces and stress to the plant material and lipid solvent, shearing cell walls and releasing botanical compounds rapidly. An exemplary sonication protocol comprises repeating high pressure and low pressure cycles, for example alternating high pressure and low pressure cycles of 20,000 times per second. Ultrasonication devices will be known to the person of ordinary skill in the art, and are available commercially, for example the Ultrasonicator UP400St from Heischler Ultrasound Technology. As a further example, the 70 W (Branson 1510 ultrasonic cleaner) can be used.

After the extraction process is completed, the solvent, which now carries the extracted cannabinoids and terpenes in solution, is drained into a cold filtration/centrifugation system, step 5 of FIG. 1. Suitable solid-liquid filtration centrifuges to filter plant biomass from solvent will be known to the person of ordinary skill in the art. For example, a Model DRC solid-liquid centrifuge available from Rousselet Robatel Kromaton can be used to separate extracted plant material from liquid solvent.

The output solvent may be returned to the reservoir container and recirculated to extraction chambers to increase the amount of cannabinoids, terpenes, and/or flavonoids. In some embodiments, the output solvent can be returned to the reservoir chamber and fresh plant material extracted at least 2×, 3×, 4×, 5×, 6×, 7×, 8×, 9×, 10× or more times.

Evaporation is intended to remove solvent from the mixture, step 6. For example, solvent can be removed by rotary evaporation, which distributes the solvent as thin film across the interior of a vessel at elevated temperature and reduced pressure. Suitable rotary evaporators will be readily apparent to the person of ordinary skill in the art, for example the KNF RC600 Rotary Evaporator System from Sterlitech.

Additional unwanted waxy material can be removed by cold filtration or centrifugation, as shown at step 7 of FIG. 1.

In some embodiments, additional purification methods, such as high performance liquid chromatography (HPLC), or molecular distillation, can be applied to the botanical extract to achieve higher purity of bioactive molecules. This purification of *cannabis* extract into cannabinoid distillates may be performed in one or more embodiments under vacuum about 0.001 mbar or by other methods, such as HPLC, step 7.

Decarboxylation

In some embodiments, *cannabis* plant material used in the extraction methods described herein is decarboxylated. Decarboxylation is a chemical reaction that converts an acid to a phenol, and releases carbon dioxide ($CO_2$), thereby removing a carbon atom from a carbon chain. Most cannabinoids exist as acids and neutral (i.e. decarboxylated) forms. Phytocannabinoids are synthesized in the plant as acid forms. Some decarboxylation does occur in the *cannabis* plant. However, decarboxylation increases significantly after the plant is harvested, and the kinetics of decarboxylation increase at higher temperatures than found in vivo.

All methods of decarboxylation known in the art are envisaged as within the scope of the instant disclosure. Exemplary decarboxylation methods are described in U.S. Pat. No. 7,344,736, the contents of which are incorporated herein by reference in their entirety.

The decarboxylation step may be carried out prior to or after extraction with organic solvent.

In some embodiments, the decarboxylation step is carried out prior to extraction with organic solvent and is conducted by heating the *cannabis* plant material to temperatures and for times which ensure at least 95% conversion of the acid cannabinoids from the acid form to their neutral form, while ensuring thermal degradation of THC to CBN is less than 10%.

Decarboxylation of cannabinoid acids is a function of time and temperature, thus at higher temperatures a shorter period of time will be taken for complete decarboxylation of a given amount of cannabinoid acid. In selecting appropriate conditions for decarboxylation consideration must, however, be given to minimizing thermal degradation of the desirable, pharmacological cannabinoids into undesirable degradation products, for example thermal degradation of THC to cannabinol (CBN).

In some embodiments, decarboxylation is carried out in a multi-step heating process in which the plant material is first heated to a first temperature for a first (relatively short) time period to evaporate off retained water and allow for uniform heating of the plant material; and second the temperature is increased to a second temperature for a second time period (typically longer than the first time period) until at least 95% conversion of the acid cannabinoids to their neutral form has occurred.

In some embodiments, the first step is conducted at a temperature in the range of 100° C. to 110° C. for 10-20 minutes. In some embodiments, the first temperature is about 105° C. and the first time period is about 15 minutes.

If the plant material is derived from *cannabis* plants having a high CBD content, the second temperature can be in the range from 115° C. to 125° C., for example about 120° C. and the second time period is in the range from 45 to 75 minutes, for example about 60 minutes. In some embodiments, the second temperature is in the range from 135° C. to 145° C., for example 140° C. and the second time period is in the range from 15 to 45 minutes, for example about 30 minutes.

If the plant material is derived from *cannabis* plants having a high THC content, the second temperature is can be in the range of 115° C. to 125° C., for example 120° C., and the second time period can be in the range of 45 minutes to 75 minutes, for example about 60 minutes. In some embodiments, the second temperature is in the range of 100° C. to 110° C., for example 105° C., and the second time period is in the range of 60 to 120 minutes.

In some embodiments, the decarboxylation step is conducted at temperatures and for times which ensure at least 97% conversion of the acid cannabinoids to their neutral form, while ensuring thermal degradation of THC to CBN is less than 5%.

In some embodiments, decarboxylation is carried out in 2 steps, for example 105° C. for 15 minutes, and then at 110° C. for about 40 to about 70 minutes.

In some embodiments, decarboxylation is carried out in a single step heating process in which the plant material is heated to between about 115 C. to 145° C. In some embodiments, decarboxylation is carried out in a single step heating process in which the plant material is heated to between about 110° C. to 145° C. In some embodiments, decarboxylation is carried out at about 110° C. or 115° C. In some embodiments the plant material is heated to between about 110° C. to 145° C. for less than 15 minutes, less than 30 minutes, less than 45 minutes, less than 60 minutes, less than 75 minutes, less than 90 minutes, less than 105 minutes or less than 120 minutes. In some embodiments the plant material is heated to between about 110° C. to 145° C. for less than one hour. In some embodiments the plant material is heated to between about 110° C. to 145° C. for between about 30 and 60 minutes.

In some embodiments, the decarboxylation step is carried out after extraction with organic solvent.

Bleaching

In some embodiments, the methods described herein comprise bleaching the botanical extract. As used herein, "bleaching" refers to a process of removing undesired minor impurities from a botanical extract, such as color pigments, free fatty acids, peroxides, undesired odor causing compounds and non-fatty materials.

In some embodiments, bleaching comprises contacting the botanical extract with a bleaching agent. Exemplary bleaching agents include natural earth clay, bentonite, acid activated clay, silica gel, diatomaceous earth, bleaching earth, activated carbon, mixtures of magnesium oxide and alumina zeolitic, or combinations thereof. For example, the botanical extract can be filtered through a cake of bleaching agent and a filter using a vacuum.

Winterizing and De-Waxing

In some embodiments, the methods of preparing a *cannabis* extract described herein comprise winterization and/or de-waxing. Winterization and de-waxing are methods to remove undesired *cannabis* lipids and waxes from *cannabis* extracts. Winterization can be achieved by dissolving a non-polar substance (e.g., the cannabinoid extract) into a polar solvent (e.g. ethanol) at sub-zero temperatures. This separates waxes and lipids from the cannabinoid extract, forcing them to collect at the top of the mixture for easy filtration.

An exemplary winterization method is described in U.S. Pat. No. 7,344,736. Ethanol is added to the *cannabis* extract in the ratio of 2:1 ethanol volume to weight. The ethanolic solution is then cooled to −20° C.±5° C. and held at this temperature for approximately 48 hours. On completion of the winterization, the precipitated waxes and lipids are removed by cold filtration through a 20 μm filter.

De-waxing also uses low temperatures to separate waxes and lipids from *cannabis* extract. In de-waxing, *cannabis* extract mixed with a solvent such as butane is cooled to low temperatures (e.g. −20° C. or below) which makes the waxes and lipids insoluble in the butane solution. Once the waxes and undesired lipids have separated from the solvent, the mixture is passed through a variety of micron screens, effectively filtering out all undesired waxes and lipids. An exemplary de-waxing protocol comprises chilling the *cannabis* extract and butane composition to low temperatures, then running the composition through a Buchner funnel that is attached to a passive vacuum, thus filtering out waxes and lips and producing a pure final product. The filtered product is then passed to a heated chamber where the butane can be removed through evaporation.

Purification of Botanical Extracts

Additional purification methods that can be applied to *cannabis* extracts produced using the methods described herein will be known to the person of ordinary skill in the art.

Exemplary additional purification methods are described in EP 1385595 B1 and U.S. Pat. No. 7,344,736, the contents of which are incorporated by reference in their entirety.

In some embodiments, partially purified botanical extracts may be further purified by chromatographic separation. High performance liquid chromatography (HPLC) is an analytical technique for determination and assay of constituents and can be used in preparative mode to produce quantities of concentrated fractions and individual components. HPLC uses pumps to pass a pressurized liquid solvent containing the botanical extract through a column filled with a solid adsorbent material. Each component of the botanical extract, such as different terpenes, flavonoids or cannabinoids, interacts slightly differently with the adsorbent material, causing different flow rates for the different components and leading to the separation of the components as they flow out of the column. However, HPLC is subject to limitations of scale as a production technique and there remains a need for additional methods of separation to produce large-scale quantities of plant extracts of sufficient quality for formulation into pharmaceutical dosage forms.

In some embodiments, distillation and/or sublimation can be used to further purify *cannabis* extracts of the instant disclosure. Distillation and sublimation have been used to separate components of plant medicines which have boiling points at or around the temperature at which water boils at atmospheric pressure (100° C.). Separation by distillation is a physical process widely used in the preparation of essential oils. For example, GB 635,121 describes a process for the preparation of extracts from aromatic plants by distillation with the help of a hot gas, preferably under high vacuum. As a further example, WO 99/11311 describes a vaporizer for inhalation and a method for the extraction of active ingredients from a crude natural product. This method utilizes an ascending stream of hot air, or a heated inert gas stream, to volatilize components from the natural product. The resultant vapor may then be inhaled by a user. As yet a further example, WO00/25127 is concerned with a method of preparing tetrahydrocannabinol using extraction of plant material with a non-polar solvent followed by vacuum distillation and collection of a constant boiling fraction. Additional distillation steps and chromatographic steps, including HPLC, reverse phase HPLC and flash chromatography, may be performed.

In some embodiments, molecular distillation can be used to further purify *cannabis* extracts of the instant disclosure. Molecular distillation, sometimes called short path distillation, is a separation technique that separates compounds through a process of slow thermal heating. The compounds in *cannabis* extracts, such as cannabinoids, terpenes and flavonoids, have different vapor pressure points (boiling points). Through precise temperature control of the distillation process, molecular distillation can separate a *cannabis* extract into one or more high-purity fractions. In exemplary embodiments, the final materials produced through short path distillation include one or more cannabinoids, one or more terpenes, and optionally, any leftover waxes, sugars, and heavy residues. In some embodiments, the molecular distillation comprises more than one round of molecular distillation.

In some embodiments, *cannabis* extracts produced by the methods of the instant disclosure can be further purified using column chromatography. Column chromatography is a method use to separate compounds based on differential absorption of the compounds to the adsorbent packed in a column. The compounds, such as different terpenes, flavonoids and cannabinoids move through the column at different rates, allowing them to be separated into fractions. The column chromatography can be carried out using any known packing material including, for example, silica or alumina for normal phase operation or $Ci\beta$ or $C\beta$ bonded phase silica for reversed phase operation. Elution of the normal phase chromatography column is carried out with solvents having an increasing polarity. Non-polar solvents include the lower straight chain and branched chain alkanes, including, for example, pentane, hexane, isooctane and petroleum ether. More polar solvents include various organic ethers, alcohols, esters or ketones, including, for example dialkyl ethers, lower alkyl acetates, lower dialkyl ketones and lower alkanols. Illustrative polar solvents include, for example, acetone, ethyl acetate, diethylether and isopropyl alcohol. The ratio of non-polar solvent to polar solvent can vary between 100:0 to 80:20.

Botanical Extracts and Compositions

The disclosure provides botanical extracts produced using the methods described herein. The botanical extracts can comprise at least one bioactive molecule derived from *cannabis*, such as cannabinoids, terpenes or flavonoids, and a solvent. Alternatively, or in addition, the botanical extracts produced using the methods described herein may be formulated as resins.

As used herein, a "botanical extract" refers to a composition comprising components extracted from plant material.

In some embodiments, the botanical extract comprises a resin. In some embodiments, the resin comprises one or more cannabinoids. In some embodiments, the resin comprises one or more cannabinoids and one or more terpenes. In some embodiments, the resin comprises one or more cannabinoids, one or more terpenes and/or one or more flavonoids.

In some embodiments, the botanical extract comprises a solid, for example a precipitate or crystalized form or the extract. In some embodiments, the botanical extract is a powder. Powders of the botanical extracts of the disclosure can be generated by methods such as spray drying, or by the addition of a plating agent or other additive that can act as a carrier. Spray drying is a method of producing a powder from a liquid or slurry by rapidly drying with hot gas. Exemplary plating agents include N-ZORBIT 2144 DG. In some embodiments, the botanical extract is formulated as a powder and comprises a plating agent or carrier. Powders of desired particle size can be generated by milling, which subjects particles to mechanical stress, breaking the particles into smaller sizes.

In some embodiments, the botanical extract comprises a liquid, for example a liquid comprising one or more cannabinoids or other bioactive molecules extracted from *cannabis* and an organic solvent. In some embodiments, the botanical extract comprises one or more cannabinoids, one or more terpenes and an organic solvent. In some embodiments, the botanical extract comprises one or more cannabinoids, one or more flavonoids and an organic solvent. In some embodiments, the botanical extract comprises one or more cannabinoids, one or more terpenes, one or more flavonoids and an organic solvent.

In some embodiments, the botanical extract comprises at least 75%, at least 80%, at least 90%, at least 95%, at least 96%, at least 97%, at least 98%, at least 98%, or at least 99% total cannabinoids.

The disclosure provides compositions comprising the botanical extracts produced using the methods described herein. The disclosure provides compositions comprising (a) a *cannabis* extract produced using the methods described herein, wherein the extract comprises at least one cannabinoid, and (b) a pharmaceutically acceptable carrier, diluent or excipient.

In some embodiments, the at least one cannabinoid comprises $\Delta^9$-tetrahydrocannabinol (THC), cannabidiol (CBD), tetrahydrocannabinolic acid (THCA), cannabidiolic acid (CBDA), cannabigerolic acid (CBGA), cannabichromenenic acid (CBCA), cannabigerovarinic acid (CBGVA), tetrahydrocanabivarinic acid (THCVA), cannabidivarinic acid (CBDVA), cannabichromevarinic acid (CBCVA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol Monomethyl Ether (CBGM), cannabielsoin (CBE), cannabicitran (CBT), or a combination thereof.

In some embodiments, the at least one cannabinoid comprises a combination of THC, THCA, CBD and CBDA.

In some embodiments, the at least one cannabinoid comprises a combination of THC and CBD.

In some embodiments, the at least one terpene comprises myrcene, terpinolene, β-caryophyllene, selina-3 7(11)-diene, Guaiol, 10-epi-y-Eudesmol, β-Eudesmol, α-Eudesmol, Bulnesol, α-Bisabolol or a combination thereof.

In some embodiments, the at least one flavonoid comprises cannflavin A, cannflavin B, cannflavin C, vitexin, isovitexin, apigenin, kaempferol, quercetin, luteolin, orientin or a combination thereof.

In some embodiments, the composition comprises about 2% to about 50% cannabinoids, about 2% to about 20% cannabinoids, about 2% to about 40% cannabinoids, about 2% to about 30% cannabinoids, about 2% to about 20% cannabinoids, about 2% to about 15% cannabinoids, about 5% to about 50% cannabinoids, about 5% to about 20% cannabinoids, about 5% to about 40% cannabinoids, about 5% to about 30% cannabinoids, about 5% to about 20% cannabinoids, about 5% to about 15% cannabinoids, about 10% to about 50% cannabinoids, about 10% to about 20% cannabinoids, about 10% to about 40% cannabinoids, about 10% to about 30% cannabinoids, about 10% to about 20% cannabinoids or about 10% to about 15% cannabinoids.

In some embodiments, the composition comprises about 2% to 20% cannabinoids. In some embodiments, the composition comprises about 5% to 20% cannabinoids. In some embodiments, the composition comprises about 5% to 15% cannabinoids.

In some embodiments, the composition comprises at least one cannabinoid and a pharmaceutically acceptable carrier, diluent or excipient. In some embodiments, the composition comprises at least one cannabinoid, at least one terpene, and a pharmaceutically acceptable carrier, diluent or excipient. In some embodiments, the composition comprises at least one cannabinoid, at least one terpene, at least one flavonoid and a pharmaceutically acceptable carrier, diluent or excipient. In some embodiments, the at least one terpene comprises myrcene, terpinolene, β-caryophyllene, selina-3 7(11)-diene, guaiol, 10-epi-y-eudesmol, β-eudesmol, α-eudesmol, bulnesol, α-bisabolol or a combination thereof. In some embodiments, the at least one flavonoid comprises cannflavin A, cannflavin B, cannflavin C, vitexin, isovitexin, apigenin, kaempferol, quercetin, luteolin, orientin or a combination thereof.

In some embodiments, the composition comprises an antioxidant such as alpha-tocopherol, a mixture of tocopherols, or rosemary extract.

In some embodiments, the composition comprises a pharmaceutically acceptable carrier, diluent or excipient. In some embodiments, the pharmaceutically acceptable carrier, diluent or excipient comprises a lipid solvent.

Exemplary lipid solvents include, but are not limited to fish oil, flax seed oil, camelina oil, evening primrose (EPO) oil, ahiflower seed oil, hemp seed oil, black currant oil, or a combination thereof.

In some embodiments, the lipid solvent comprises omega-3 fatty acids. In some embodiments, the lipid solvent comprises monoacylglycerides, diacyglycerides and phospholipids. In some embodiments, the omega-3 fatty acids are omega-3 monoacylglycerides, omega-3 diacyglycerides, omega-3 phospholipids or a combination thereof.

As used herein, "glycerides", also known as "acyglycerols", refers to a class of molecules where esters are formed between a glycerol and a fatty acid. An "acylglyceride linkage" refers to the covalent bond between the organic acid group, such as a fatty acid, and one of the three hydroxyl groups of the glycerol, for example via an ester linkage.

As used herein, "monoacylglycerides", or "MAG", sometimes also referred to as "monoglycerides" or "monoacylglycerols" are a class of glycerides which are composed of a molecule of glycerol linked to a fatty acid via an ester bond. Glycerol contains both primary and secondary alcohol groups. Therefore, two different types of monoglycerides may be formed: 1-monoacylglycerols where the fatty acid is attached to a primary alcohol, and 2-monoacylglycerols where the fatty acid is attached to the secondary alcohol.

"Diacylglycerides", or "DAG", sometimes referred to as "diglyceride" or "diacylglycol", refers to a glyceride consisting of two fatty acids covalently linked to a glycerol molecule through ester linkages. Two possible forms exist: 1,2-diacylglycerols and 1,3-diacylglycerols.

"Triglycerides", sometimes referred to as "TG", "TAG", "triacylglycerol" or "triacylglyceride" are molecules comprising a glycerol linked to three fatty acids via esters.

The term "fatty acid(s)" as used herein refers to long chain aliphatic acids (alkanoic acids) of varying chain lengths, from about C12 to C22 (although both longer and shorter chain-length acids are known). For example, the predominant chain lengths are about C16 to about C22. The structure of a fatty acid is represented by a simple notation system of "X:Y", where X is the total number of carbon (C) atoms and Y is the number of double bonds.

Generally, fatty acids are classified as saturated or unsaturated. The term "saturated fatty acids" refers to those fatty acids that have no "double bonds" between their carbon backbone. In contrast, "unsaturated fatty acids" are cis-isomers that have "double bonds" along their carbon backbones. "Monounsaturated fatty acids" have only one "double bond" along the carbon backbone (e.g., usually between the 9th and 10th carbon atom as for palmitoleic acid (16:1) and oleic acid (18:1)), while "polyunsaturated fatty acids" (or "PUFAs") have at least two double bonds along the carbon backbone (e.g., between the 9th and 10th, and 12th and 13th carbon atoms for linoleic acid (18:2); and between the 9th and 10th, 12th and 13th, and 15th and 16th for [alpha]-linolenic acid (18:3)).

PUFAs can be classified into two major families (depending on the position (n) of the first double bond nearest the methyl end of the fatty acid carbon chain). Thus, the "[omega]-6 fatty acids" [omega]-6 or n-6) have the first unsaturated double bond six carbon atoms from the omega (methyl) end of the molecule and additionally have a total of two or more double bonds, with each subsequent unsaturation occurring 3 additional carbon atoms toward the carboxyl end of the molecule. In contrast, the "[omega]-3 fatty acids" ([omega]-3 or n-3) have the first unsaturated double bond three carbon atoms away from the omega end of the molecule and additionally have a total of three or more double bonds, with each subsequent unsaturation occurring 3 additional carbon atoms toward the carboxyl end of the molecule.

A "saturated fatty acid" or "SFA" is a type of fat in which the fatty acid chains have all, or predominantly all, single bonds.

As used herein, "omega-3 fatty acids", also called "ω-3 fatty acids" or "n-3 fatty acids" refers to polyunsaturated fatty acids (PUFAs) that are characterized by the presence of a double bond three atoms away from the terminal methyl group of the fatty acid. Exemplary omega-3 fatty acids include α-linolenic acid (ALA) found in plant oils, and eicosapentaenoic acid (EPA) and docosahexaenoic acid (DHA), both commonly found in marine oils. Common sources of plant oils containing ALA include walnut, edible seeds, clary sage seed oil, algal oil, flaxseed oil, Sacha Inchi oil, Echium oil, and hemp oil. Common sources of animal omega-3 fatty acids EPA and DHA include fish, fish oils, eggs from chickens fed EPA and DHA, and squid oils.

A "lipid" is a molecule that is soluble in nonpolar solvents. Lipids include fats, fatty acids and their derivatives, as well as sterol-containing metabolites such as cholesterols and waxes.

A "phospholipid" refers to a class of lipid comprising two hydrophobic fatty acid tails and a hydrophilic head comprising a phosphate group, which can be joined together via a glycerol molecule. The phosphate groups of the head can be modified with organic molecules such as choline, ethanolamine or serine.

An "omega-3 containing phospholipid" is a phospholipid where one or both of the fatty acid tails of the phospholipid is an omega-3 fatty acid.

In some embodiments, the lipid solvent comprises polyunsaturated fatty acids (PUFA). In some embodiments, the lipid solvent comprises saturated fatty acids (SFA). In some embodiments, the lipid solvent comprises PUFA and SFA. As used herein, the PUFA/SFA index refers to the ratio of PUFA to SFA in the lipid solvent. In some embodiments, the lipid solvent comprises a PUFA/SFA index of at least 7, at least 8, at least 9, at least 10, at least 20, at least 30, at least 40, at least 50, at least 60, at least 70, at least 80, at least 90, at least 100, at least 110, at least 120, at least 130, at least 140 or at least 150.

In some embodiments, the lipid solvent comprises omega-3 fatty acids (5-3). Exemplary omega-3 fatty acids include alpha-linolenic acid (ALA), eicosapentaenoic acid (EPA), and docosahexaenoic acid (DHA). ALA is found mainly in plant oils such as flaxseed, soybean, and canola oils. DHA and EPA are found in fish and other seafood. In some embodiments, at least 10%, at least 15%, at least 20%, at least 30%, at least 35%, at least 40%, at least 50%, at least 55%, at 60%, at least 65%, at least 70%, at least 75%, at least 80%, at least 85%, at least 86%, at least 87%, at least 88%, at least 89%, at least 90%, at least 95% or at least 95% of the fatty acids in the lipid solvent are omega-3 fatty acids.

In some embodiments, the lipid solvent comprises fish oil, flax seed oil, camelina oil, evening primrose (EPO) oil, ahiflower seed oil, hemp seed oil, black currant oil, or a combination thereof. In some embodiments, the lipid solvent comprises monoacylglycerides (MAG) and/or diacylglycerides (DAG). In some embodiments, the monoacylglycerides (MAG) and/or diacylglycerides (DAG) are complexed with omega-3 fatty acids. In some embodiments, monoacylglycerides (MAG) and/or diacylglycerides (DAG) are complexed with polyunsaturated omega-3 fatty acids. In fish oils, MAG and DAG are naturally present in trace amounts. However, in concentrated fish oils that have converted ethyl ester fatty acids to TAG fatty acids (known as re-esterified triglycerides), the amount of MAG and DAG in the product can be higher due to incomplete enzymatic or chemical reactions. In some embodiments, for example those embodiments where the lipid solvent comprises an animal oil, the lipid solvent comprises about 1% to about 3% MAG. In some embodiments, for example those embodiments where the lipid solvent is a plant oil, the lipid solvent comprises about 0.2% to about 3% MAG. In some embodiments, the lipid solvent comprises less than 3%, less than 2.5%, less than 2%, less than 1.5%, less than 1%, less than 0.5%, less than 0.4%, less than 0.3%, less than 0.2%, or less than 0.1% MAG.

In some embodiments, the lipid solvent comprises about 0.5% to about 40% DAG. In some embodiments, for example those embodiments where the lipid solvent comprises an animal oil, the lipid solvent comprises about 1% to about 40% DAG. In some embodiments, for example those embodiments where the lipid solvent comprises a plant oil, the lipid solvent comprises between 0.5% to about 7% DAG. In some embodiments, the lipid solvent comprises less than 40%, less than 30%, less than 20%, less than 10%, less than 9%, less than 8%, less than 7%, less than 6%, less than 5%, less than 4%, less than 3%, less than 2%, less than 1%, less than 0.7%, less than 0.5%, less than 0.3%, or less than 0.2% DAG. In some embodiments, the lipid solvent comprises a fish oil, and the fish oil comprises between about 1% and about 3% MAG, and between about 1% and about 40% DAG. In some embodiments, the lipid solvent comprises a vegetable oil, and the vegetable oil comprises between about 0.2% and about 3.0% MAG, and between about 0.5% and about 7.0% DAG.

TABLE 1

Fatty acid profiles of exemplary oils with a freezing point below −5° C.

| Oil Type | Solvent Name | ω-3 (as % FA) | % MAG; % DAG[2] | PUFA/SFA Index | Freezing Point |
|---|---|---|---|---|---|
| Animal Oil | EE Fish Oil | 88 | 1-3% MAG; | 46.3 | −40° C. |
|  | RTG Fish Oil | 75 | 1-40% DAG | ≥100 |  |
| Flax seed oil (from different sources) | Omega Nutrition flax seed oil | 55 | 0.2-3% MAG; 0.5-7% DAG | 8.9 | −24° C. |
|  | TAFOODs flax seed oil | 57 |  | 10.7 |  |
|  | Shape Foods High ALA Flax oil | 66 |  | 10.1 |  |
|  | Shape Foods Organic Cold press | 57 |  | 9.1 |  |
| Camelina[1] oil | Camelina oil | 35 |  | 7.3 | −15° C. |
| EPO oil | EPO oil | ≥9 |  | 10.3 | −20° C. |
| Ahiflower seed oil | Natures Crops Ahiflower oil | 66 |  | 11.5 | −20° C. |
| Hemp seed oil | Hemp seed oil Chii | 18 |  | 8.2 | −8° C. |
| Black currant oil | Black currant oil | 15 |  | 9.1 | −20° C. |

Abbreviations:
ω, omega;
ALA, alpha-linolenic acid;
DAG, diacylglyceride;
EPO, evening primrose oil;
FA, fatty acid;
MAG, monoacylglyceride;
PUFA, polyunsaturated fatty acid;
RTG, re-esterified triglyceride;
SFA, saturated fatty acid
[1]Data from Health Canada
[2]indicates percent glycerides that are MAG and that are DAG Any pharmaceutically acceptable carrier, diluent or excipient known in the art can be used in the *cannabis* extract compositions described herein. Examples of pharmaceutically acceptable carriers, diluents and excipients for oral delivery include: sodium bicarbonate solutions and similar diluents which neutralize stomach acid or have similar buffering capacity, glycols, oils or emulsions; and include formulations in the form of gels, pastes and viscous colloidal dispersions. The *cannabis* extract compositions may be presented in capsule, tablet, slow release or elixir form or as a gel or paste. Furthermore, the *cannabis* extract compositions may be presented as a food or drink.

Suitable carriers or diluents illustratively include, but are not limited to, either individually or in combination, lactose, including anhydrous lactose and lactose monohydrate; starches, including directly compressible starch and hydrolyzed starches; mannitol; sorbitol; xylitol; dextrose and dextrose monohydrate; dibasic calcium phosphate dihydrate; sucrose-based diluents; confectioner's sugar; monobasic calcium sulfate monohydrate; calcium sulfate dihydrate; granular calcium lactate trihydrate; dextrates; inositol; hydrolyzed cereal solids; amylose; celluloses including microcrystalline cellulose, food grade sources of alpha- and amorphous cellulose, powdered cellulose, and hydroxypropylmethylcellulose (HPMC); calcium carbonate; glycine; bentonite; block co-polymers; polyvinylpyrrolidone; and the like.

*Cannabis* extract compositions of the disclosure optionally comprise one or more pharmaceutically acceptable disintegrants as excipients, particularly for tablet formulations. Suitable disintegrants include, but are not limited to, either individually or in combination, starches, including sodium starch glycolate and pregelatinized corn starches, celluloses such as purified cellulose, microcrystalline cellulose, methylcellulose, carboxymethylcellulose and sodium carboxymethylcellulose, croscarmellose sodium, alginates, crospovidone, and gums such as agar, guar, locust bean, karaya, pectin and tragacanth gums.

*Cannabis* extract compositions of the disclosure optionally comprise one or more pharmaceutically acceptable binding agents or adhesives as excipients, particularly for tablet formulations. Such binding agents and adhesives preferably impart sufficient cohesion to the powder being tableted to allow for normal processing operations such as sizing, lubrication, compression and packaging, but still allow the tablet to disintegrate and the composition to be absorbed upon ingestion. Suitable binding agents and adhesives include, but are not limited to, either individually or in combination, acacia; tragacanth; sucrose; gelatin; glucose; starches such as, but not limited to, pregelatinized starches; celluloses such as, but not limited to, methylcellulose and carmellose sodium Tylose; alginic acid and salts of alginic acid; magnesium aluminum silicate; polyethylene glycol (PEG); guar gum; polysaccharide acids; bentonites; povidone, for example povidone K-15, K-30 and K-29/32; polymethacrylates; hydroxypropylcellulose; and ethylcellulose.

Polymeric binding agents can have varying molecular weight, degrees of crosslinking, and grades of polymer. Polymeric binding agents can also be copolymers, such as block copolymers that contain mixtures of ethylene oxide and propylene oxide units. Variation in these units' ratios in a given polymer affects properties and performance. Examples of block co-polymers with varying compositions of block units are Poloxamer 188 and Poloxamer 237 (BASF Corporation).

*Cannabis* extract compositions of the disclosure optionally comprise one or more pharmaceutically acceptable wetting agents as excipients. Non-limiting examples of surfactants that can be used as wetting agents in *cannabis* extract compositions of the disclosure include quaternary ammonium compounds, for example benzalkonium chloride, benzethonium chloride and cetylpyridinium chloride, dioctyl sodium sulfosuccinate, polyoxyethylene alkylphenyl ethers, for example nonoxynol 9, nonoxynol and octoxynol 9, poloxamers (polyoxyethylene and polyoxypropylene block copolymers, polyoxyethylene fatty acid glycerides and oils, for example polyoxyethylene caprylic/capric mono- and diglycerides, polyoxyethylene, castor oil and polyoxyethylene, hydrogenated castor oil; polyoxyethylene alkyl ethers, for example polyoxyethylene cetostearyl ether, polyoxyethylene fatty acid esters, for example polyoxyethylene stearate, polyoxyethylene sorbitan esters, for example polysorbate and polysorbate, Tween 80, propylene glycol fatty acid esters, for example propylene glycol laurate, sodium lauryl sulfate, fatty acids and salts thereof, for example oleic acid, sodium oleate and triethanolamine oleate, glyceryl fatty acid esters, for example glyceryl monostearate, sorbitan esters, for example sorbitan monolaurate, sorbitan monooleate, sorbitan monopalmitate and sorbitan monostearate, tyloxapol, and mixtures thereof.

*Cannabis* extract compositions of the disclosure optionally comprise one or more pharmaceutically acceptable lubricants (including anti-adherents and/or glidants) as excipients. Suitable lubricants include, but are not limited to, either individually or in combination, glyceryl behapate (Compritol 888); stearic acid and salts thereof, including magnesium, calcium and sodium stearates; hydrogenated vegetable oils; colloidal silica; talc; waxes; boric acid; sodium benzoate; sodium acetate; sodium fumarate; sodium chloride; DL-leucine; PEG Carbowax; sodium oleate; sodium lauryl sulfate; and magnesium lauryl sulfate.

Suitable anti-adherents include, but are not limited to, talc, cornstarch, DL-leucine, sodium lauryl sulfate and metallic stearates.

Glidants can be used to promote powder flow of a solid formulation. Suitable glidants include, but are not limited to, colloidal silicon dioxide, starch, talc, tribasic calcium phosphate, powdered cellulose and magnesium trisilicate. Colloidal silicon dioxide is particularly preferred. Other excipients such as colorants, flavors and sweeteners are known in the pharmaceutical art and can be used in *Cannabis* extract compositions of the instant disclosure. Tablets can be coated, for example with an enteric coating, or uncoated. Compositions of the invention can further comprise, for example, buffering agents.

*Cannabis* extract compositions of the instant disclosure may also contain additives, such as water, alcohols, oils (mineral, vegetable, animal and synthetics), glycols, colorants, preservatives, emulsifiers, gelling agents, gums, esters, hormones, steroids, anti-oxidants, silicones, polymers, fragrances, flavors, other active ingredients, acids, bases, buffers, vitamins, minerals, salts, polyols, proteins and their derivatives, essential oils, other enzymes, co-enzymes and extracts, surfactants, detergents, soaps, anionics, non-ionics, ionics, waxes, lipids, stabilizers, fillers, celluloses, glycans, amines, solubilizers, thickeners, sugars and sugar derivatives, ceramides, sweeteners and the like, so long as such additives do not defeat the objectives of the present invention.

*Cannabis* extract compositions of the disclosure may be formulated for topical administration. For example, *cannabis* extract compositions may be formulated as a liquid, gel, cream, ointment, lotion, salve, balm or paste. Topical formulations can comprise pharmaceutically acceptable carriers, solvents, adhesives, dispersion agents and the like. Topical formulations can be formulated for application to intact skin or mucous membranes, and have a highly localized effect.

*Cannabis* extract compositions of the disclosure may be formulated for transmucosal administration, parenteral administration, subdermal administration, or inhalation. For example, *cannabis* extract compositions can be injected intravenously or under the skin (subcutaneously, or subdermal administration).

*Cannabis* extract compositions of the disclosure may be formulated for transmucosal administration. For example, transmucosal administration can encompass oral formulations for buccal administration, and aerosol sprays for nasal administration and/or inhalation.

*Cannabis* extract compositions of the disclosure may be formulated for inhalation. For example, *cannabis* extract compositions can be formulated as vapors or aerosols that can be inhaled into the lungs. Vapor formulations include liquid formulations that are vaporized when loaded into a suitable vaporization device.

Antioxidants

The disclosure provides compositions comprising a *cannabis* extract, a lipid-based carrier and an antioxidant.

In some embodiments, the anti-oxidant is a fat-soluble antioxidant. Antioxidants are compounds that inhibit oxidation, a chemical reaction that can produce free radicals, which can cause cellular damage.

In some embodiments, the antioxidant comprises alpha tocopherol, a mixture of tocopherols, or rosemary extract. Exemplary tocopherols include d-α-tocopheryl acetate, d-α-tocopheryl acid succinate, d-β-tocopherol, d-β-tocopherol, d-γ-tocopherol, d-δ-tocopherol, d-α-tocotrienol, d-β-tocotrienol, d-γ-tocotrienol, d-δ-tocotrienol, dl-α-tocopherol, dl-α-tocopheryl acetate, dl-α-tocopheryl calcium succinate, dl-α-tocopheryl nicotinate, dl-α-tocopheryl linoleate/oleate and all other possible stereo isomeric forms of the above compounds, and are sometimes referred to as "Vitamin E." Additional anti-oxidants include beta-carotene, carotenoids, and Vitamin A.

In some embodiments, the composition is formulated for oral administration. An oral composition according to the instant disclosure may be in any of the dosage forms which are generally used for dietary supplements such as liquids, gels, powders, tablets, caplets, capsules, gelcaps, food additives, drops, beverages, pills, lozenges, rinses, pastes, gums and soft gels.

Compositions of the instant disclosure may also contain additives, such as water, alcohols, oils (mineral, vegetable, animal and synthetics), glycols, colorants, preservatives, emulsifiers, gelling agents, gums, esters, hormones, steroids, anti-oxidants, silicones, polymers, fragrances, flavors, other active ingredients, acids, bases, buffers, vitamins, minerals, salts, polyols, proteins and their derivatives, essential oils, other enzymes, co-enzymes and extracts, surfactants, detergents, soaps, anionics, non-ionics, ionics, waxes, lipids, stabilizers, fillers, celluloses, glycans, amines, solubilizers, thickeners, sugars and sugar derivatives, ceramides, sweeteners and the like, so long as such additives do not defeat the objectives of the present invention.

Methods of Making *Cannabis* Extract Compositions

The disclosure provides methods of making the compositions comprising the botanical extract described herein. In some embodiments, the methods comprise (a) providing a *cannabis* extract produced using the methods described herein; and (b) mixing the *cannabis* extract with a pharmaceutically acceptable carrier, diluent or excipient. In some embodiments, the methods comprise mixing the *cannabis* extract and the pharmaceutically acceptable carrier with one or more antioxidants.

In some embodiments, *cannabis* extract comprises a liquid or a resin.

In some embodiments, the *cannabis* extract is formulated with a pharmaceutically acceptable carrier, diluent or excipient. The pharmaceutically acceptable carrier, diluent or excipient can be a liquid, for example a liquid comprising fish oil, flax seed oil, camelina oil, evening primrose oil, black current oil, ahiflower seed oil, or a combination thereof.

In some embodiments, the *cannabis* extract is mixed with the pharmaceutically acceptable carrier, diluent or excipient at a ratio of about 1:7, about 1:8, about 1:9, about 1:9.5, about 1:10, about 1:11, about 1:12, about 1:13, about 1:14, about 1:15, about 1:16, about 1:17, about 1:18, about 1:19, about 1:20, about 1:21, about 1:22, about 1:23, about 1:24, or about 1:25 *cannabis* extract to pharmaceutically acceptable carrier. In some embodiments, the *cannabis* extract is mixed with the pharmaceutically acceptable carrier at a ratio of about 1:9 *cannabis* extract to pharmaceutically acceptable carrier.

OTHER EMBODIMENTS

While the invention has been described in conjunction with the detailed description thereof, the foregoing description is intended to illustrate and not limit the scope of the invention, which is defined by the scope of the appended claims. Other aspects, advantages, and modifications are within the scope of the following.

EXAMPLES

Example 1: Extraction of Dry *Cannabis* with Cold Ethanol

Step 1: 10 grams (g) of dry frozen crushed *cannabis* flowers from strain Nebula, with 10% CBD+CBDA and 5.6% THC+THCA by weight percent, were placed in an open vessel.

Step 2: 250 milliliters (ml) of ethanol at −20° C. was added to the same vessel.

Step 3: The contents of said vessel were stirred at cold temperature (−20° C.) for about 30 minutes.

Step 4: The contents were then cold-filtered or cold-centrifuged at 100×g for 5 min to remove solid materials.

Step 5: Rotary evaporation was used to separate solvent from the mixture.

Optional Step: Steps 2 to 4 can be repeated until the concentration of cannabinoids in the solvent reaches the target. Table 2 illustrates the relative extraction efficiency of active ingredients of dry cold crushed Nebula flowers with cold ethanol during 30 minutes.

Optional Step: Additional purification methods can be applied to the extract produced by Steps 1-5.

TABLE 2

Relative extraction efficiency (%) of active ingredients of dry cold crushed Nebula flowers with Cold Ethanol during 30 minutes.

| Parameter | THCA + THC | CBDA + CBD | Total cannabinoids | Terpenes | Purity |
|---|---|---|---|---|---|
| Ethanol at −20° C., 30 minutes | 98.9 | 82.5 | 88.5 | 151.2 | 82.9 |

The control extraction was done with Methanol/Chloroform (9:1). Extraction efficiency (%) is relative to the control extraction.

Example 2: Extraction of Dry *Cannabis* with Cold Acetone

Step 1: 10 g of dry frozen crushed *cannabis* flowers from strain Nebula, with 10% CBD+CBDA and 5.6% THC+THCA by weight percent, were placed in an open vessel.

Step 2: 250 ml of acetone at −20° C. was added to the same vessel.

Step 3: The contents of said vessel were stirred at cold temperature (−20° C.) for about 10 minutes.

Step 4: The contents were then cold-filtered or cold-centrifuged at 100×g for 5 min to remove solid materials.

Step 5: Rotary evaporation was used to separate solvent from the mixture.

Optional Step: Steps 2 to 4 can be repeated until the concentration of cannabinoids in the solvent reaches the target. Table 3 illustrates the extraction efficiency of active ingredients of dry cold crushed Nebula flowers with cold acetone during 10 minutes.

Optional Step: Additional purification methods can be applied on the extract.

TABLE 3

Relative extraction efficiency (%) of active ingredients of dry cold crushed Nebula flowers with Cold Acetone during 10 minutes.

| Parameter | THCA + THC | CBDA + CBD | Total cannabinoids | Terpenes | Purity |
|---|---|---|---|---|---|
| Acetone at −20° C., 10 minutes | 96.8 | 81.0 | 86.7 | 192.1 | 84.5 |

The control extraction was done with Methanol/Chloroform (9:1). Extraction efficiency (%) is relative to the control extraction.

Example 3: Extraction of Dry *Cannabis* with Cold Acetone

Step 1: 10 g of dry frozen crushed *cannabis* flowers from strain Nebula, with 10% CBD+CBDA and 5.6% THC+THCA by weight percent, were placed in an open vessel.

Step 2: 250 ml of acetone −20° C. was added to the same vessel.

Step 3: The contents of said vessel were stirred at cold temperature (−20° C.) for about 10 minutes.

Step 4: An ultrasound device 70 W (Branson 1510 ultrasonic cleaner) was used in the vessel during the extraction. With power ultrasound, *cannabis* extraction is faster and highly efficient.

Step 5: The contents of the vessel were then cold-filtered or cold-centrifuged at 100×g for 5 min to remove solid materials.

Step 6: Rotary evaporation was used to separate solvent from the mixture.

Optional Step: Steps 2 to 5 can be repeated until the concentration of cannabinoids in the solvent reaches the target. Table 4 illustrates the extraction efficiency of active ingredients of dry cold crushed Nebula flowers with cold acetone (−20° C.) during 10 minutes with ultrasound.

Optional Step: Additional purification methods can be applied to the extract.

TABLE 4

Relative extraction efficiency (%) of active ingredients of dry cold crushed Nebula flowers with Cold Acetone during 10 minutes assisted with ultrasound (U/S).

| Parameter | THCA + THC | CBDA + CBD | Total cannabinoids | Terpenes | Purity |
|---|---|---|---|---|---|
| Acetone at −20° C., 10 minutes | 92.6 | 87.1 | 89.5 | 204.1 | 91.7 |

The control extraction was done with Methanol/Chloroform (9:1). Extraction efficiency (%) is relative to the control extraction.

Example 4: Extraction of Dry *Cannabis* with Cold Acetone

Step 1: 10 g of dry frozen crushed *cannabis* flowers from strain Nebula, with 10% CBD+CBDA and 5.6% THC+THCA by weight percent, were placed in an open vessel.

Step 2: 250 ml of acetone at −50° C. was added to the same vessel.

Step 3: The contents of said vessel were stirred at cold temperature (−50° C.) for about 10 minutes.

Step 4: An ultrasound device 70 W (Branson 1510 ultrasonic cleaner) was used in the extraction vessel. With power ultrasound, *cannabis* extraction is faster and highly efficient.

Step 5: The contents of the vessel were then cold-filtered or cold-centrifuged at 100×g for 5 min to remove solid materials.

Step 6: Rotary evaporation was used to separate solvent from the mixture.

Optional Step: Steps 2 to 5 can be repeated until the concentration of cannabinoids in the solvent reaches the target. Table 5 illustrates the extraction efficiency of active ingredients of dry cold crushed Nebula flowers with cold acetone (−50° C.), with 10 minutes with ultrasound.

Optional Step: Additional purification methods can be applied to the extract.

TABLE 5

Relative extraction efficiency (%) of active ingredient of dry cold crushed Nebula flowers with −50° C. Acetone during 10 minutes assisted with ultrasound (U/S).

| Parameter | THCA + THC | CBDA + CBD | Total cannabinoids | Terpenes | Purity |
|---|---|---|---|---|---|
| Acetone at −50° C., 10 minutes with ultrasound | 93.2 | 81.5 | 86.1 | 90.4 | 90.4 |

The control extraction was done with Methanol/Chloroform (9:1). Extraction efficiency (%) is relative to the control extraction.

Example 5: Extraction of Fresh *Cannabis* with Cold Ethanol

Step 1: 10 g of fresh frozen crushed *cannabis* flowers from strain Nebula, with 10% CBD+CBDA and 5.6% THC+THCA by weight percent, were placed in an open vessel.

Step 2: 250 ml of ethanol at −20° C. was added to the same vessel.

Step 3: The contents of said vessel were stirred at cold temperature (−20° C.) for about 30 minutes.

Step 4: The content was then cold-filtered or cold-centrifuged at 100×g for 5 min to remove solid materials.

Step 5: Rotary evaporation was used to separate solvent from the mixture

Optional Step: Step 2 to 4 can be repeated until the concentration of cannabinoids in the solvent reaches the target. Table 6 illustrates the extraction efficiency of active ingredients of fresh cold crushed Nebula flowers with cold ethanol (−20° C.), during 30 minutes.

Optional Step: Additional purification methods can be applied to the extract.

TABLE 6

Relative extraction efficiency (%) of active ingredients of fresh cold crushed Nebula flowers with Cold Ethanol during 30 minutes.

| Parameter | THCA + THC | CBDA + CBD | Total cannabinoids | Terpenes | Purity |
|---|---|---|---|---|---|
| Ethanol at −20° C., 30 minutes | 98.7 | 90.9 | 93.5 | 3.1 | 65.7 |

The control extraction was done with Methanol/Chloroform (9:1). Extraction efficiency (%) is relative to the control extraction.

Example 6: Extraction of Dry *Cannabis* with Cold Ethyl Acetate

Step 1: In order to decarboxylate the *cannabis* plant material, 200 g of whole flower *cannabis* was placed at 105° C. for 15 minutes, and then at 110° C. for 1 hour. After cooling, the plant material was ground. Table 7 illustrates the cannabinoid concentration in dry crushed and dry decarboxylated crushed Nebula flowers.

TABLE 7

Cannabinoids concentration (g/100 g dry material) in dry crushed and dry decarboxylated crushed Nebula flowers

| Biomass | THCA | THC | CBDA | CBD | Total Cannabinoids |
|---|---|---|---|---|---|
| Ground Nebula | 3.7 | 0.8 | 8.4 | 0.8 | 12.8 |
| Ground Decarboxylated Nebula | 0.1 | 4.0 | 2.1 | 6.8 | 12.9 |

Total cannabinoids are expressed as neutral form.

Step 2: 10 g of dry decarboxylated crushed cannabis flowers from strain Nebula, with 8.9% CBD+CBDA and 4.1% THC+THCA by weight percent, were placed in an open vessel.

Step 3: 250 ml of ethyl acetate at −20° C. was added to the same vessel.

Step 4: The contents of said vessel were stirred at cold temperature (−20° C.) for about 30 minutes.

Step 5: The contents of the vessel were then cold-filtered or cold-centrifuged at 100×g for 5 min to remove solid materials.

Step 6: Rotary evaporation was used to separate solvent from the mixture.

Optional Step: Steps 3 to 5 can be until the concentration of cannabinoids in the solvent reaches the target. Table 8 illustrates the extraction efficiency of active ingredients of dry cold decarboxylated crushed Nebula flowers with cold ethyl acetate (−20° C.), during 30 minutes.

Optional Step: Additional purification methods can be applied to the extract.

TABLE 8

Relative extraction efficiency (%) of active ingredients of dry cold decarboxylated crushed Nebula flowers with Cold Ethyl Acetate during 30 minutes.

| Parameter | THCA + THC | CBDA + CBD | Total cannabinoids | Terpenes | Purity |
|---|---|---|---|---|---|
| Ethyl Acetate at −20° C., 30 minutes | 101.2 | 101.3 | 101.5 | 83.2 | 78.4 |

The control extraction was done with Methanol/Chloroform (9:1). Extraction efficiency (%) is relative to the control extraction.

Example 7: Chlorophyll Content of Organic Solvent Extracts

Dry cannabis flowers contain large amounts of chlorophyll, which can be undesirable in cannabis extracts.

Chlorophyll cold extraction was performed on dry, cold cannabis material with acetone, ethanol or ethyl acetate as described above. The control extraction used Methanol/Chloroform (9:1) as extraction solvent, as in preceding examples.

Figure 6:
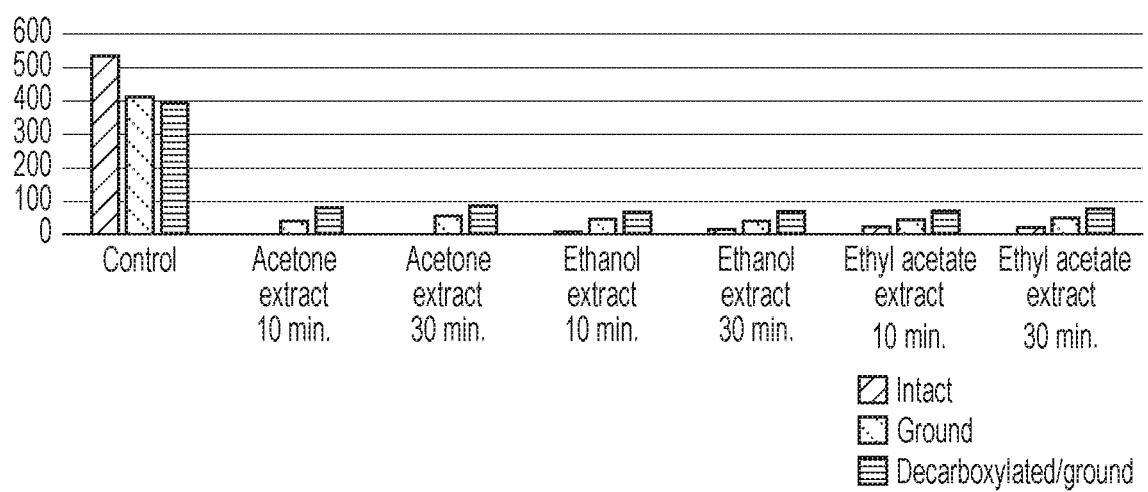
FIG. 6 is a plot showing chlorophyll content in cold extracts in relation to the extraction solvents used. Chlorophyll cold extraction was performed on dry, cold *cannabis* material with acetone, ethanol or ethyl acetate. Results are expressed as ppm. The control extraction used Methanol/Chloroform (9:1) as extraction solvent.

Extraction with cold organic solvent greatly reduces chlorophyll extraction, as shown on FIG. 6. Results are expressed in ppm (mg/kg dry cannabis).

What is claimed is:

1. A method of preparing a cannabis extract comprising:
   a. providing cannabis plant material comprising stems, leaves, seeds, flowers or a combination thereof in an extraction chamber;
   b. contacting an organic solvent at a temperature of between about 0° C. and −80° C. with the cannabis plant material;
   c. extracting at least one bioactive molecule from the cannabis plant material into the organic solvent for a first period of time, thereby producing an organic solvent comprising a cannabis extract, wherein the extraction step takes place at between about 0° C. and −80° C.;
   d. filtering or centrifuging the organic solvent and the cannabis plant material to remove solid materials; and
   e. recovering the cannabis extract from the organic solvent; thereby producing the cannabis extract.

2. The method of claim 1, wherein the cannabis plant material is heated to a temperature of between 110 to 145° C. prior to step (a).

3. The method of claim 2, wherein the cannabis plant material is heated for about 40 to 75 minutes.

4. The method of claim 1, wherein the first period of time is no more than 1 hour.

5. The method of claim 1, comprising sonicating the organic solvent and the cannabis plant material for a second period of time, wherein the second period of time occurs:
   (1) prior to step (c), or
   (2) during step (c), and is the same as the first period of time.

6. The method of claim 5, wherein the second period of time is about 10 minutes.

7. The method of claim 1, wherein the organic solvent is at a temperature of between about 0° C. and −70° C., about 0° C. and −60° C., about 0° C. and −50° C., about 0° C. and −40° C., about 0° C. and −30° C., about 0° C. and −20° C., about 0° C. and −10° C., about −10° C. and −80° C., about −10° C. and −60° C., about −10° C. and −50° C., about −10° C. and −40° C., about −20° C. and −60° C., or about −20° C. and −50° C.

8. The method of claim 1, wherein the organic solvent is selected from the group consisting of ethanol, acetone, and ethyl acetate.

9. The method of claim 1, comprising returning the organic solvent comprising the cannabis extract from step (d) to the extraction chamber and repeating steps (b) through (d).

10. The method of claim 9, wherein un-extracted cannabis plant material is added to the extraction chamber prior to repeating steps (c) and (d).

11. The method of claim 1, wherein step (e) comprises evaporation of the organic solvent.

12. The method of claim 1, wherein the cannabis extract is subject to one or more additional purification methods.

13. The method of claim 12, wherein the one or more additional purification methods comprise molecular distillation or high-performance liquid chromatography (HPLC).

14. The method of claim 1, wherein the cannabis plant material is Cannabis sativa, Cannabis indica, Cannabis ruderalis or a hybrid thereof.

15. The method of claim 1, wherein the cannabis plant material is industrial hemp.

16. The method of claim 1, wherein the at least one bioactive molecule comprises a cannabinoid, a flavonoid or a terpene.

17. The method of claim 16, wherein the cannabinoid comprises $\Delta^9$-tetrahydrocannabinol (THC), cannabidiol (CBD), tetrahydrocannabinolic acid (THCA), cannabidiolic acid (CBDA), cannabigerolic acid (CBGA), cannabichromenenic acid (CBCA), cannabigerovarinic acid (CBGVA), tetrahydrocanabivarinic acid (THCVA), cannabidivarinic acid (CBDVA), cannabichromevarinic acid (CBCVA), cannabinol (CBN), cannabigerol (CBG), cannabichromene (CBC), cannabicyclol (CBL), cannabivarin (CBV), tetrahydrocannabivarin (THCV), cannabidivarin (CBDV), cannabichromevarin (CBCV), cannabigerovarin (CBGV), cannabigerol monomethylether (CBGM), cannabielsoin (CBE), cannabicitran (CBT), or a combination thereof.

18. The method of claim 16, wherein the cannabinoid comprises THC, THCA, CBD, CBDA or a combination thereof.

19. A method of making a *cannabis* extract composition, comprising:
   a. providing the *cannabis* extract produced by the method of claim 1, and
   b. mixing the *cannabis* extract with a pharmaceutically acceptable carrier, diluent or excipient.

20. The method of claim 19, wherein the composition is formulated as a liquid, gel, softgel, powder, tablet, caplet, capsule, gelcap, food additive, drop, beverage, pill, lozenge, rinse, paste gum, cream, ointment, lotion, salve, balm or paste.

* * * * *